(12) United States Patent
Shuey et al.

(10) Patent No.: US 7,307,061 B2
(45) Date of Patent: Dec. 11, 2007

(54) β-PEPTOIDS WITH ANTIMICROBIAL ACTIVITY

(75) Inventors: Steven W. Shuey, Landenberg, PA (US); William J. Delaney, Bear, DE (US); Mukesh C. Shah, Hockessin, DE (US); Mark A. Scialdone, West Grove, PA (US)

(73) Assignee: E.I. du Pont de Nemours and Company, Wilmington, DE (US)

( * ) Notice: Subject to any disclaimer, the term of this patent is extended or adjusted under 35 U.S.C. 154(b) by 0 days.

(21) Appl. No.: 11/311,097

(22) Filed: Dec. 19, 2005

(65) Prior Publication Data
US 2006/0160735 A1 Jul. 20, 2006

Related U.S. Application Data

(60) Provisional application No. 60/640,903, filed on Dec. 30, 2004.

(51) Int. Cl.
*A61K 38/04* (2006.01)
(52) U.S. Cl. .......................................... 514/2
(58) Field of Classification Search ...................... None
See application file for complete search history.

(56) References Cited

OTHER PUBLICATIONS

Tossi et al., "Design of synthetic antimicrobial peptides based on sequence analogy and amphipathicity," Eur. J. Biochem., 1997, 250, 549-58.*
Jean-Luc Fauchere et. al., Differential Protection and Selective Deprotection in Peptide Synthesis, The Peptides, 1981, pp. 203-253, vol. 3.
Bruce C. Hamper et. al., Solid Phase Synthesis of B-Peptoids: N-Substituted B-Aminopropionic Acid Oligomers, J. Org. Chem., 1998, pp. 708-718, vol. 63.
Sankar Chatterjee et. al., Synthesis and Biological Activity of a Series of Potent Fluoromethyl Ketone Inhibitors of Recombinant Human Calpain I, J. Med. Chem., 1997, pp. 3820-3828, vol. 40.
Rozalyn A. Simon et. al., One-Bead-One-Compound Library of End-Capped Dipeptides and Deconvolution by Microflow NMR, J. Comb. Chem., 2005, pp. 697-702, vol. 7.

* cited by examiner

*Primary Examiner*—Cecilia J. Tsang
*Assistant Examiner*—Christina M. Bradley

(57) ABSTRACT

The present invention relates to beta-peptoids with antimicrobial activity. The present invention also relates to methods of producing β-peptoids. The antimicrobial β-peptoids of the invention are useful in pharmaceutical, healthcare, medical device, industrial, food, agricultural, and personal care applications.

10 Claims, 4 Drawing Sheets

β-PEPTOIDS WITH ANTIMICROBIAL ACTIVITY

This application claims the benefit of U.S. Provisional Application Ser. No. 60/640,903, filed Dec. 30, 2004.

FIELD OF THE INVENTION

The present invention relates to beta-peptoids with antimicrobial activity. The present invention also relates to methods of producing β-peptoids. The antimicrobial β-peptoids of the invention are useful in pharmaceutical, healthcare, medical device, industrial, food, agricultural, and personal care applications.

TECHNICAL BACKGROUND OF THE INVENTION

Antimicrobial peptides are ubiquitous in nature and play an important role in the innate immune system of many species. Many antimicrobial peptides are cationic, amphiphilic compounds that are believed to act by inducing pore formation in cell membranes. Antimicrobial peptides exhibit a broad spectrum of activity against microbes, and are believed to be immune to the development of resistance due to their non-specific mode of action. Peptides, however, are subject to proteolytic degradation and thus considerable effort has been devoted to synthesizing peptide mimetics, such as peptides comprised of D-isomers of amino acids, β-peptides and α-peptoids, which would be more stable to enzymatic hydrolysis.

β-Peptoids are N-substituted oligo-β-alanines (N-substituted β-aminopropionic acids) that were first described by Hamper, et al. (J. Org. Chem. (1998) 63:708-718). β-Peptoids are known to form random structures with high conformational freedom due to the absence of backbone hydrogen bonding. In addition, the tertiary amides of β-peptoids provide a backbone structure that is expected to be more stable to chemical or enzymatic hydrolysis than peptides.

Hamper, et al. (supra) described a method for the solid-phase synthesis of β-peptoids from a two-step, iterative reaction of resin-bound acrylate or acrylamides with primary amines followed by acryloylation of the resultant secondary amine with an acrylic acid derivative to regenerate the acrylamide. This method of synthesis was used to prepare β-peptoids comprising one to three N-substituted β-alanine residues. The antimicrobial activity of the β-peptoids synthesized by Hamper, et al., however, or of β-peptoids in general, is not known. The present invention provides novel β-peptoid polymers having antimicrobial activity.

SUMMARY OF THE INVENTION

The present invention provides β-peptoids according to Formula I:

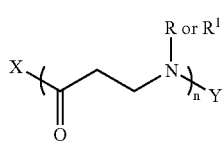

Formula I comprised of monomers according to Formula II:

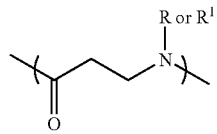

Formula II wherein the R or $R^1$ side-chain of each monomer is independently selected and a) R is selected from the group consisting of:
(i) $CH_3$, $C_2H_5$, or $C_3$ to $C_{12}$ straight-chain, branched or cyclic alkane or alkene;
(ii) $C_6$ to $C_{20}$ unsubstituted aryl or unsubstituted heteroaryl, wherein one or more heteroatoms are independently selected from the group consisting of O, N and S;
(iii) $C_6$ to $C_{20}$ substituted aryl or substituted heteroaryl, wherein one or more heteroatoms are independently selected from the group consisting of O, N and S; and one or more substituents are independently selected from the group consisting of 1) Cl, 2) Br, 3) F, 4) $CH_3$, 5) $C_2H_5$, 6) $C_3$ to $C_{12}$ straight-chain, branched or cyclic alkane or alkene; 7) O-alkane or O-alkene, wherein alkane or alkene is selected from the group consisting of $CH_3$, $C_2H_5$, and $C_3$ to $C_{12}$ straight-chain or branched alkane or alkene, 8) OH, and 9) SH;

b) $R^1$ is selected from the group consisting of:
(iv) $A$-$NR^2R^3$, wherein A is selected from the group consisting of:
$CH_3$;
$C_2H_5$;
$C_3$ to $C_{12}$ straight-chain, branched or cyclic alkane or alkene;
$C_6$ to $C_{20}$ unsubstituted aryl or unsubstituted heteroaryl, wherein one or more heteroatoms are independently selected from the group consisting of O, N and S;
$C_6$ to $C_{20}$ substituted aryl or substituted heteroaryl, wherein one or more heteroatoms are independently selected from the group consisting of O, N and S, and one or more substituents are independently selected from the group consisting of 1) Cl, 2) Br, 3) F, 4) $CH_3$, 5) $C_2H_5$, 6) $C_3$ to $C_{12}$ straight-chain, branched or cyclic alkane or alkene; 7) O-alkane or O-alkene, wherein alkane or alkene is selected from the group consisting of $CH_3$, $C_2H_5$, and $C_3$ to $C_{12}$ straight-chain or branched alkane or alkene, 8) OH, and 9) SH;
and $R^2$ and $R^3$ are independently selected from the group consisting of:
H;
$CH_3$;
$C_2H_5$;
$C_3$ to $C_6$ straight-chain, branched or cyclic alkane or alkene;
$C_6$ to $C_{20}$ unsubstituted aryl or unsubstituted heteroaryl, wherein one or more heteroatoms are independently selected from the group consisting of O, N and S;
$C_6$ to $C_{20}$ substituted aryl or substituted heteroaryl, wherein one or more heteroatoms are independently selected from the group consisting of O, N and S, and one or more substituents are independently selected from the group consisting of 1) Cl, 2) Br, 3) F, 4) $CH_3$, 5) $C_2H_5$, 6) $C_3$ to $C_{12}$ straight-chain, branched or cyclic alkane or alkene; 7) O-alkane or O-alkene, wherein alkane or alkene is selected from the group consisting of $CH_3$, $C_2H_5$, and $C_3$ to $C_{12}$ straight-chain or branched alkane or alkene, 8) OH, and 9) SH; and optionally $R^2$ and $R^3$ can together form a cyclic or bicyclic alkanyl or alkenyl group;

(v) A-NHC=NHNH$_2$, wherein A is defined as in step (iv);

(vi) unsubstituted A-pyridyl, wherein A is defined as in step (iv);

(vii) substituted A-pyridyl wherein A is defined as in step (iv), and one or more substituents are independently selected from the group consisting of 1) Cl, 2) Br, 3) F, 4) $CH_3$, 5) $C_2H_5$, 6) $C_3$ to $C_{12}$ straight-chain, branched or cyclic alkane or alkene; 7) O-alkane or O-alkene, wherein alkane or alkene is selected from the group consisting of $CH_3$, $C_2H_5$, and $C_3$ to $C_{12}$ straight-chain or branched alkane or alkene, 8) OH, and 9) SH;

(viii) amidine having the Formula A-(C=N)NH$_2$, wherein A is defined as in step (iv);

(ix) unsubstituted A-imidazole wherein A is defined as in step (iv); and (x) substituted A-imidazole wherein A is defined as in step (iv), and one or more substituents are independently selected from the group consisting of 1) Cl, 2) Br, 3) F, 4) $CH_3$, 5) $C_2H_5$, 6) $C_3$ to $C_{12}$ straight-chain, branched or cyclic alkane or alkene; 7) O-alkane or O-alkene, wherein alkane or alkene is selected from the group consisting of $CH_3$, $C_2H_5$, and $C_3$ to $C_{12}$ straight-chain or branched alkane or alkene, 8) OH, and 9) SH;

c) X is selected from the group consisting of OH, NH$_2$ and an amino acid;

d) Y is selected from the group consisting of:
(xi) H;
(xii) a group having the Formula:

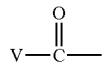

wherein V is selected from the group consisting of $CH_3$, $C_2H_5$, $C_3$ to $C_7$ straight-chain, branched or cyclic alkane or alkene, and benzoyl;

(xiii) a group having the Formula

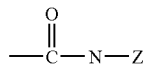

wherein Z is selected from the group consisting of:
$CH_3$;
$C_2H_5$;
$C_3$ to $C_6$ straight-chain, branched or cyclic alkane or alkene;
$C_6$ to $C_{20}$ unsubstituted aryl or unsubstituted heteroaryl, wherein one or more heteroatoms are independently selected from the group consisting of O, N and S; and
$C_6$ to $C_{20}$ substituted aryl or substituted heteroaryl, wherein one or more heteroatoms are independently selected from the group consisting of O, N and S, and one or more substituents are independently selected from the group consisting of 1) Cl, 2) Br, 3) F, 4) $CH_3$, 5) $C_2H_5$, 6) $C_3$ to $C_{12}$ straight-chain, branched or cyclic alkane or alkene; 7) O-alkane or O-alkene, wherein alkane or alkene is selected from the group consisting of $CH_3$, $C_2H_5$, and $C_3$ to $C_{12}$ straight-chain or branched alkane or alkene, 8) OH, and 9) SH;

(xiv) a group having the Formula

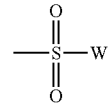

wherein W is selected from the group consisting of:
$CH_3$;
$C_2H_5$;
$C_3$ to $C_6$ straight-chain, branched or cyclic alkane or alkene;
$C_6$ to $C_{20}$ unsubstituted aryl or unsubstituted heteroaryl, wherein one or more heteroatoms are independently selected from the group consisting of O, N and S; and
$C_6$ to $C_{20}$ substituted aryl or substituted heteroaryl, wherein one or more heteroatoms are independently selected from the group consisting of O, N and S, and one or more substituents are independently selected from the group consisting of 1) Cl, 2) Br, 3) F, 4) $CH_3$, 5) $C_2H_5$, 6) $C_3$ to $C_{12}$ straight-chain, branched or cyclic alkane or alkene; 7) O-alkane or O-alkene, wherein alkane or alkene is selected from the group consisting of $CH_3$, $C_2H_5$, and $C_3$ to $C_{12}$ straight-chain or branched alkane or alkene, 8) OH, and 9) SH;

e) n is 4 to 50; and f) the ratio of monomers having R side-chains to monomers having $R^1$ side-chains in the antimicrobial polymer is from about 0.1 to about 0.8.

The present invention also provides a method for preparing a β-peptoid according to claim 1 comprising:
(i) synthesizing β-peptoid blocks of 2-5 monomers;
(ii) ligating the β-peptoid blocks of step (i) by amide bond formation. The β-peptoid blocks may be identical, or the β-peptoid blocks may be non-identical.

The present invention also provides an antimicrobial composition comprising at least one β-peptoid according to Formula 1. The present invention also provides antimicrobial substrates comprising at least one β-peptoid according to Formula 1 bound to or incorporated into a substrate; the invention also provides articles comprised of substrates of the invention.

The present invention also provides a method for killing, inhibiting, or preventing the growth of at least one microbe, the method comprising contacting the microbe with an effective amount of the β-peptoid of Formula 1.

BRIEF DESCRIPTION OF THE DRAWINGS

FIG. 1 shows the solution phase synthesis of β-peptoid blocks, wherein the values in bold indicate the β-peptoid blocks that were synthesized by the reaction.

FIG. 2 shows the solid-phase synthesis of p-peptoid blocks, wherein the values in bold indicate the β-peptoid blocks that were synthesized by the reaction.

DETAILED DESCRIPTION OF THE INVENTION

Figure 1A:
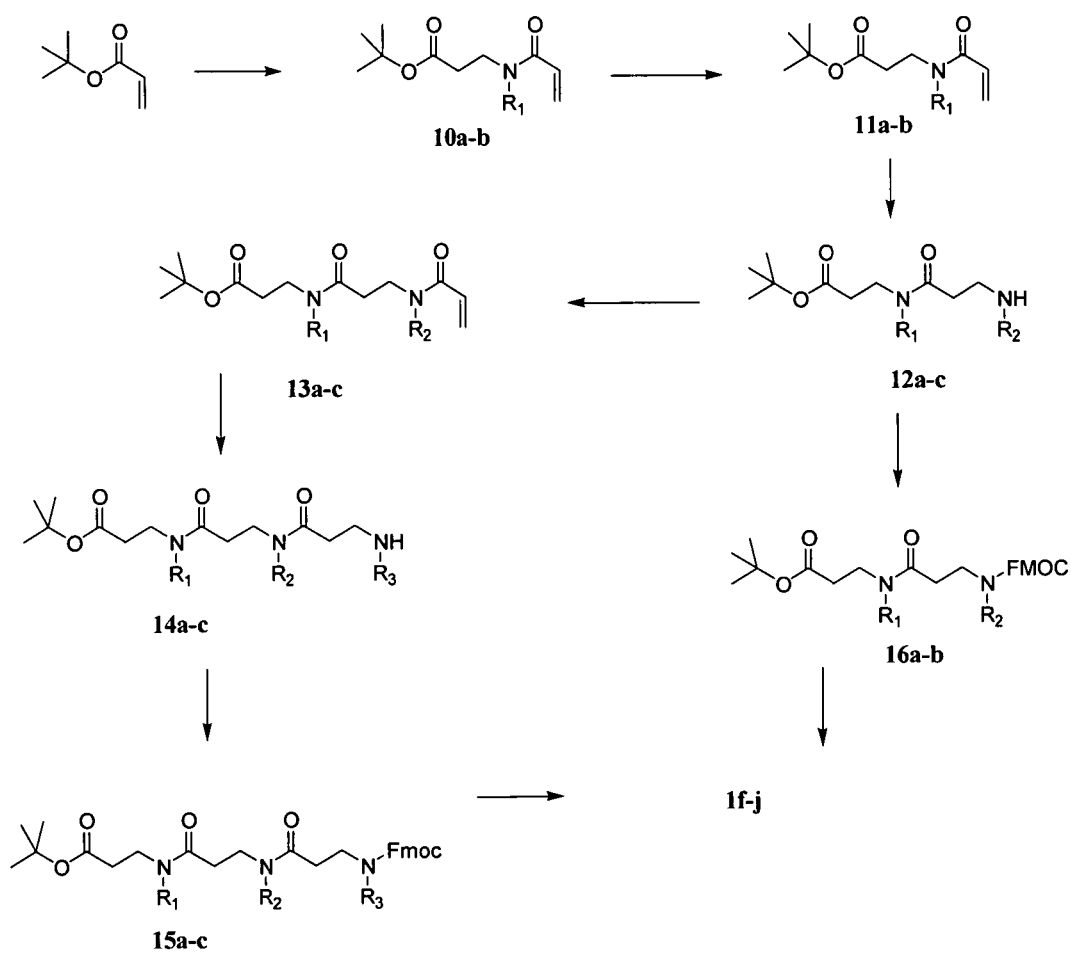
FIG. 1A shows the general scheme for the synthesis.

Applicants specifically incorporate the entire contents of all cited references in this disclosure. Further, when an amount, concentration, or other value or parameter is given as either a range, preferred range, or a list of upper preferable values and lower preferable values, this is to be understood as specifically disclosing all ranges formed from any pair of any upper range limit or preferred value and any lower range limit or preferred value, regardless of whether ranges are separately disclosed. Where a range of numerical values is recited herein, unless otherwise stated, the range is intended to include the endpoints thereof, and all integers and fractions within the range. It is not intended that the scope of the invention be limited to the specific values recited when defining a range.

The present invention provides novel β-peptoids having antimicrobial activity. The present invention also provides methods for synthesizing the β-peptoids of the invention. The invention further provides compositions comprising these antimicrobial β-peptoids and methods of use thereof for killing, reducing the growth of, or preventing the growth of microorganisms. The invention also provides substrates and articles comprising β-peptoids of the present invention.

Definitions:

In this disclosure, a number of terms are used. The following definitions are provided.

The term "alkane" refers to a saturated hydrocarbon having the general formula $C_nH_{2n+2}$, and may be straight-chain, branched or cyclic. The term "alkene" refers to an unsaturated hydrocarbon that contains one or more C=C double bonds, and may be straight-chain, branched or cyclic. An alkene requires a minimum of two carbons. A cyclic compound requires a minimum of three carbons. The term "aromatic" refers to benzene and compounds that resemble benzene in chemical behavior. "Alkaryl" refers to alkylene-aryl, where "alkylene" refers to a diradical of a branched or unbranched saturated hydrocarbon chain. Such alkaryl groups are exemplified by benzyl, phenethyl, and the like. "Heteroaryl" refers to a compound having a heteroatom. A "heteroatom" is an atom other than carbon in the structure of a cyclic or heterocyclic compound. "Heteroalkaryl" refers to an alkaryl compound having a heteroatom.

The term "pyridyl" refers to a compound having the Formula:

The term "A-pyridyl" refers to a compound wherein a group "A" as defined below is attached to any of the carbon atoms (C2 to C6). An "A-pyridyl" may be substituted on any of the carbons not used for attachment above, as described below.

The term "imidazole" refers to a compound having the Formula:

The term "A-imidazole" refers to a compound wherein a group "A" as defined below is attached on any of the e carbons. An "A-imidazole" may be substituted on any of the carbons as described below.

The term "amino acid" refers to L-amino acids, D-amino acids, and unnatural amino acids such as β-amino acids and cyclic amino acids. Unnatural amino acids may be obtained, for example, from Fluka (Buchs, Switzerland) through Sigma-Aldrich (St. Louis, Mo.).

The term "polymer" or "oligomer" or "antimicrobial polymer" of antimicrobial oligomer" refers to a macromolecule comprising a plurality of monomers of the invention. The terms "β-peptoid" or "β-peptoid oligomer" are used interchangeably and refer to antimicrobial polymers comprised of N-substituted β-aminopropionic acid monomers.

"Monomers" of the present invention have the following Formula II:

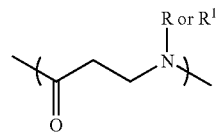

Formula II wherein R and $R^1$ are defined according to Formula I below.

The term "antimicrobial" means having to do with the killing, growth inhibition or growth prevention of microorganisms. "Growth inhibition" means reduced growth of the microorganisms. "Growth prevention" means that growth is stopped.

The term "microorganism" or "microbe" is meant to include any organism comprised of the phylogenetic domains bacteria and archaea, as well as unicellular and filamentous fungi (such as yeasts and molds), unicellular and filamentous algae, unicellular and multicellular parasites, and viruses.

The term "cytotoxic" means the killing or lysis of eukaryotic organisms.

The term "amphiphilic" refers to a peptide or peptoid with spatially segregated polar, cationic residues and non-polar residues.

A "substrate coated with an effective amount of an antimicrobial composition" means applying to the surface a composition comprising one or more antimicrobial β-peptoids in an amount effective to kill, inhibit or prevent the growth of microorganisms.

The term "MIC" refers to minimal inhibitory concentration and will be defined as the lowest concentration of either soluble β-peptoid or β-peptoid immobilized on a substrate that results in total kill of bacteria.

The present invention provides β-peptoids according to Formula I:

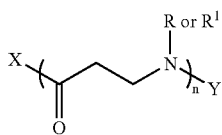

Formula I comprised of monomers according to Formula II:

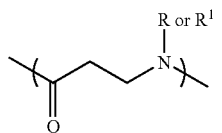

Formula II wherein the R or $R^1$ side-chain of each monomer is independently selected and a) R is independently selected from the group consisting of:
   (i) $CH_3$, $C_2H_5$, or $C_3$ to $C_{12}$ straight-chain, branched or cyclic alkane or alkene;
   (ii) $C_6$ to $C_{20}$ unsubstituted aryl or unsubstituted heteroaryl;
   (iii) $C_6$ to $C_{20}$ substituted aryl or substituted heteroaryl;

b) $R^1$ is independently selected from the group consisting of:
   (iv) $A-NR^2R^3$, wherein A is selected from the group consisting of:
       $CH_3$;
       $C_2H_5$;
       $C_3$ to $C_{12}$ straight-chain, branched or cyclic alkane or alkene;
       $C_6$ to $C_{20}$ unsubstituted aryl or unsubstituted heteroaryl;
       $C_6$ to $C_{20}$ substituted aryl or substituted heteroaryl;
       and $R^2$ and $R^3$ are independently selected from the group consisting of:
       H;
       $CH_3$;
       $C_2H_5$;
       $C_3$ to $C_6$ straight-chain, branched or cyclic alkane or alkene;
       $C_6$ to $C_{20}$ unsubstituted aryl or unsubstituted heteroaryl;
       $C_6$ to $C_{20}$ substituted aryl or substituted heteroaryl; and
       optionally $R^2$ and $R^3$ can together form a cyclic or bicyclic alkanyl or alkenyl group;
   (v) $A-NHC=NHNH_2$, wherein A is defined as in step (iv);
   (vi) unsubstituted A-pyridyl, wherein A is defined as in step (iv);
   (vii) substituted A-pyridyl wherein A is defined as in step (iv);
   (viii) amidine having the Formula $A-(C=N)NH_2$, wherein A is defined as in step (iv);
   (ix) unsubstituted A-imidazole wherein A is defined as in step (iv); and
   (x) substituted A-imidazole wherein A is defined as in step (iv);

c) X is selected from the group consisting of OH, $NH_2$ and an amino acid;

d) Y is selected from the group consisting of:
   (xi) H;
   (xii) a group having the Formula:

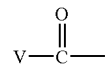

wherein V is selected from the group consisting of $CH_3$, $C_2H_5$, $C_3$ to $C_7$ straight-chain, branched or cyclic alkane or alkene, and benzoyl;

(xiii) a group having the Formula

wherein Z is selected from the group consisting of:
$CH_3$;
$C_2H_5$;
$C_3$ to $C_6$ straight-chain, branched or cyclic alkane or alkene;
$C_6$ to $C_{20}$ unsubstituted aryl or unsubstituted heteroaryl;
$C_6$ to $C_{20}$ substituted aryl or substituted heteroaryl;

(xiv) a group having the Formula

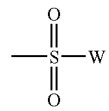

wherein W is selected from the group consisting of:
$CH_3$;
$C_2H_5$;
$C_3$ to $C_6$ straight-chain, branched or cyclic alkane or alkene;
$C_6$ to $C_{20}$ unsubstituted aryl or unsubstituted heteroaryl;
$C_6$ to $C_{20}$ substituted aryl or substituted heteroaryl;

e) n is 4 to 50; and f) the ratio of monomers having R side-chains to monomers having $R^1$ side-chains in the antimicrobial polymer is from about 0.1 to about 0.8. The ratio refers to the number of side chains within the β-peptoid.

The number of heteroatoms within a heteroaryl group is one to three; heteroatoms are independently selected from the group consisting of O, N and S.

The number of substituents on substituted aryl, substituted heteroaryl, substituted pyridyl or substituted imidazole groups is generally one to three, although additional substituents may be present; the substituents are independently selected from the group consisting of 1) Cl, 2) Br, 3) F, 4) $CH_3$, 5) $C_2H_5$, 6) $C_3$ to $C_{12}$ straight-chain, branched or cyclic alkane or alkene; 7) O-alkane or O-alkene, wherein alkane or alkene is selected from the group consisting of $CH_3$, $C_2H_5$, and $C_3$ to $C_{12}$ straight-chain or branched alkane or alkene, 8) OH, and 9) SH;

In one embodiment of the invention, the number of monomer units is 4 to 50. In a preferred embodiment of the invention, the number of monomer units is 7 to 25.

In one embodiment of the invention, the ratio of monomers having R side-chains to monomers having $R^1$ side-chains in the antimicrobial β-peptoid is from about 0.2 to about 0.6. In another embodiment of the invention, the ratio of monomers having R side-chains to monomers having $R^1$ side-chains in the antimicrobial β-peptoid is from about 0.25 to about 0.5.

Synthesis of β-peptoids

Initially, the method of Hamper, et al. (supra) was used to synthesize β-peptoids of the invention. It was discovered, however, that poor yields of the desired oligomer were obtained when longer peptoids were synthesized (i.e., greater than 5-mers). The syntheses of the present invention allow for the preparation of β-peptoid oligomers comprised of greater than 5 monomeric β-peptoid units. In addition, according to the processes of the invention, the side-chains of each monomer unit can be individually selected, thus allowing one to chemically "tune" the β-peptoid oligomers, resulting in a desired structure or chemical composition.

Two methods were developed for synthesis of the β-peptoid polymers. According to both methods, β-peptoid blocks of 2 or more, and preferably 2 to 5, β-peptoid monomers are first synthesized and orthogonally protected in a manner well known in the art for peptide synthesis. The blocks are then linked together on a solid support, by an iterative cycle (approximately 0 to 25 times) of amide bond formation and selective deprotection of the beta amine position similar to that used in peptide synthesis (as described, for example, in Bodanszky, M and Bodanszky, A "The Practice of Peptide Synthesis", 2nd ed. (Springer-Verlag, N.Y.,1994). The β-peptoid blocks may be identical, or individual β-peptoid blocks may be non-identical. For example, two or more β-peptoid blocks, each comprising different monomers, may be ligated. When the β-peptoid of desired length and chemical composition is complete, the molecule is cleaved from the support by methods well known in the art. Substantially any synthesis support useful for peptide synthesis or solid phase synthesis which links through a carboxylic acid can be used as would be well understood by people of skill in the art. Side chain protecting groups are either removed in the cleavage step or in a subsequent step prior to purification.

In one embodiment of the invention, Rink resin is used as the solid support, Boc groups are used to protect the side chains of the R and $R^1$ groups and Fmoc groups are used to protect the beta amine position. The Fmoc groups are removed in each cycle by treatment of the resin with piperidine solution, which does not affect the Boc groups. When the final desired β-peptoid is complete, the resin is treated with trifluoroacetic acid solution, simultaneously cleaving the β-peptoid from the support and removing the side chain protecting groups.

According to Method 1, liquid-phase synthesis is used to prepare short β-peptoid blocks of the desired chain length, for instance di-β-peptoids or tri-β-peptoids (di-β-peptoids and tri-β-peptoids are β-peptoids comprised of two monomers or three monomers, respectively). In Method 2, solid-phase synthesis is used to prepare short β-peptoid blocks of desired monomer length.

Figure 1B:
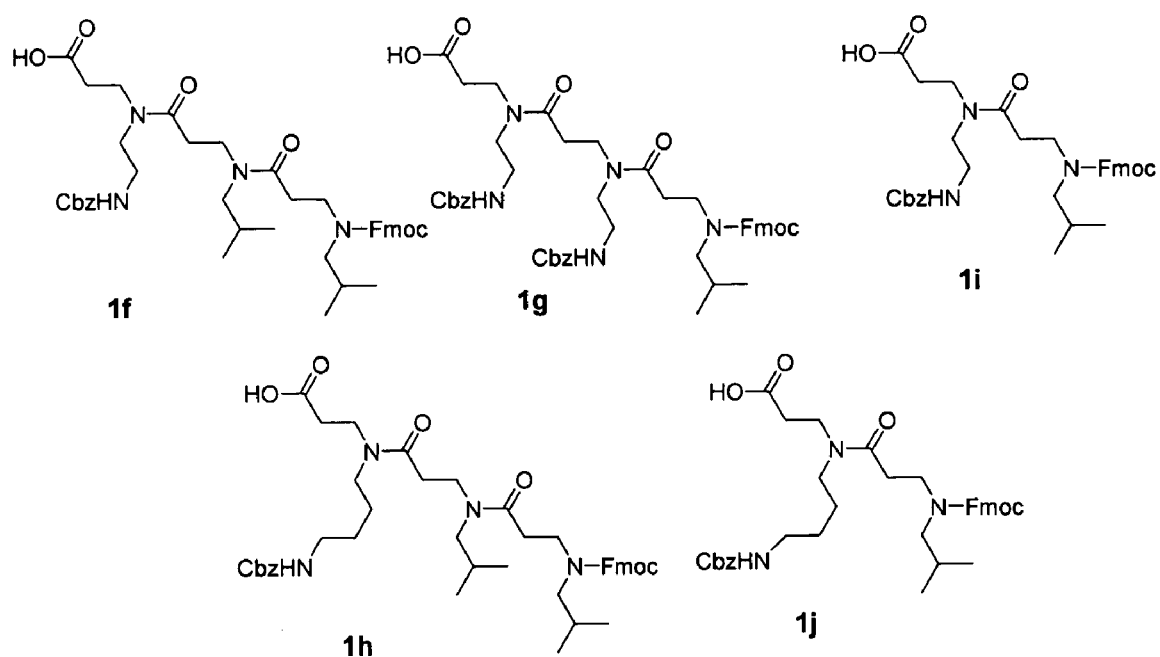
FIG. 1B shows the structure of the β-peptoid blocks that were synthesized using this method.

Method 1 t-Butyl acrylate is reacted with a primary amine in a Michael-type reaction to give beta-aminoesters (as shown in FIG. 1). Primary amines useful for the Michael reaction are those having the Formula R—$NH_2$, wherein R is at least one of the group consisting of:

(i) $CH_3$, $C_2H_5$, or $C_3$ to $C_{12}$ straight-chain, branched or cyclic alkane or alkene; $C_6$ to $C_{20}$ unsubstituted aryl or unsubstituted heteroaryl, wherein one or more heteroatoms are independently selected from the group consisting of O, N and S;

(ii) $C_6$ to $C_{20}$ substituted aryl or substituted heteroaryl, wherein one or more heteroatoms are independently selected from the group consisting of O, N and S; and one or more substituents are independently selected from the group consisting of 1) Cl, 2) Br, 3) F, 4) $CH_3$, 5) $C_2H_5$, 6) $C_3$ to $C_{12}$ straight-chain, branched or cyclic alkane or alkene; 7) O-alkane or O-alkene, wherein alkane or alkene is selected from the group consisting of $CH_3$, $C_2H_5$, and $C_3$ to $C_{12}$ straight-chain or branched alkane or alkene, 8) OH, and 9) SH.

Primary amines useful for the Michael reaction also include those having the Formula $R^1$—$NH_2$, wherein $R^1$ is at least one of the group consisting of:

(iii) A-$NR^2R^3$, wherein A is selected from the group consisting of:
  $CH_3$;
  $C_2H_5$;
  $C_3$ to $C_{12}$ straight-chain, branched or cyclic alkane or alkene;
  $C_6$ to $C_{20}$ unsubstituted aryl or unsubstituted heteroaryl, wherein one or more heteroatoms are independently selected from the group consisting of O, N and S;
  $C_6$ to $C_{20}$ substituted aryl or substituted heteroaryl, wherein one or more heteroatoms are independently selected from the group consisting of O, N and S; and one or more substituents are independently selected from the group consisting of 1) Cl, 2) Br, 3) F, 4) $CH_3$, 5) $C_2H_5$, 6) $C_3$ to $C_{12}$ straight-chain, branched or cyclic alkane or alkene; 7) β-alkane or O-alkene, wherein alkane or alkene is selected from the group consisting of $CH_3$, $C_2H_5$, and $C_3$ to $C_{12}$ straight-chain or branched alkane or alkene, 8) OH, and 9) SH;

and $R^2$ and $R^3$ are independently selected from the group consisting of:
  H;
  $CH_3$;
  $C_2H_5$;
  $C_3$ to $C_6$ straight-chain, branched or cyclic alkane or alkene;
  $C_6$ to $C_{20}$ unsubstituted aryl or unsubstituted heteroaryl, wherein one or more heteroatoms are independently selected from the group consisting of O, N and S;
  $C_6$ to $C_{20}$ substituted aryl or substituted heteroaryl, wherein one or more heteroatoms are independently selected from the group consisting of O, N and S; and one or more substituents are independently selected from the group consisting of 1) Cl, 2) Br, 3) F, 4) $CH_3$, 5) $C_2H_5$, 6) $C_3$ to $C_{12}$ straight-chain, branched or cyclic alkane or alkene; 7) O-alkane or O-alkene, wherein alkane or alkene is selected from the group consisting of $CH_3$, $C_2H_5$, and $C_3$ to $C_{12}$ straight-chain or branched alkane or alkene, 8) OH, and 9) SH; and optionally $R^2$ and $R^3$ can together form a cyclic or bicyclic alkanyl or alkenyl group;

(v) A-NHC=$NHNH_2$, wherein A is defined as in step (iv);
(vi) unsubstituted A-pyridyl, wherein A is defined as in step (iv);
(vii) substituted A-pyridyl wherein A is defined as in step (iv), and one or more substituents are independently selected from the group consisting of 1) Cl, 2) Br, 3) F, 4) $CH_3$, 5) $C_2H_5$, 6) $C_3$ to $C_{12}$ straight-chain, branched or cyclic alkane or alkene; 7) O-alkane or O-alkene, wherein alkane or alkene is selected from the group consisting of $CH_3$, $C_2H_5$, and $C_3$ to $C_{12}$ straight-chain or branched alkane or alkene, 8) OH, and 9) SH;

(viii) amidine having the Formula A-(C=N)NH$_2$, wherein A is defined as in step (iv);

(ix) unsubstituted A-imidazole wherein A is defined as in step (iv); and (x) substituted A-imidazole wherein A is defined as in step (iv), and one or more substituents are independently selected from the group consisting of 1) Cl, 2) Br, 3) F, 4) $CH_3$, 5) $C_2H_5$, 6) $C_3$ to $C_{12}$ straight-chain, branched or cyclic alkane or alkene; 7) O-alkane or O-alkene, wherein alkane or alkene is selected from the group consisting of $CH_3$, $C_2H_5$, and $C_3$ to $C_{12}$ straight-chain or branched alkane or alkene, 8) OH, and 9) SH.

Those skilled in the art will recognize that protecting groups may be required for amines used in the Michael Addition reactions of the invention. Examples include side-chain protecting groups such as benzyloxycarbonyl (Boc) and carbobenzoxy (Cbz). A detailed description of protecting groups can be found in Merrifield, B., Solid Phase Synthesis (Peptides: Synthesis, Structures and Applications, Gutte, B. (ed.) (1995) Academic Press, NY, pages 93-169). The addition of protecting groups is exemplified in the present invention for the synthesis of Compounds 17 and 19. Michael Addition reactions are well known to those skilled in the art. The reactions may be carried out at a temperature of from about 0° C. to about 150° C., generally for a time of several minutes to about 48 hours. The temperature and time may be adjusted to achieve optimal yield of the β-aminoester product. The molar ratio of t-butyl acrylate to primary amine ranges from about 1:2 to about 1:20. In one embodiment of the invention, the molar ratio of t-butyl acrylate to primary amine is approximately 1:10. Solvents useful for the reaction include inert solvents such as methanol, isopropanol, dimethyl sulfoxide, and 1,4-dioxane. The β-aminoester product may be purified by removal of the solvent by, for example, rotary evaporation, followed by removal of excess reactants.

The β-aminoesters are then reacted with acryloyl chloride to give N-substituted acrylamides. The reaction is carried out at a temperature of from about −20° C. to about 25° C. The reaction is carried out in an inert solvent, such as tetrahydrofuran. The reaction may be catalyzed by 4-dimethylaminopyridine. The molar ratio of acryloyl chloride to β-aminoester is from about 1:1 to about 1:2. The solvent may be removed by rotary evaporation. The resultant product may be purified by standard methods, such as extraction and flash chromatography.

The cycle of 1) Michael-type addition followed by 2) reaction with acryloyl chloride may be iteratively repeated 0-4 times to give blocks of the desired length. The side-chains of the amines may be varied so as to achieve a desired chemical content. When the desired block is complete, the terminal secondary amine functionality is protected with a suitable group such as 9-fluorenylmethoxycarbonyl (FMOC) to give orthogonally protected building blocks, as is commonly used in peptide synthesis (Fauchere, J. and Schwyzer, R. (1981) In "The Peptides" E. Gross and J. Meienhofer, eds., Vol. 3, p. 203-253 Academic Press, NY). The t-butyl ester group can be removed from the carboxyl end of the β-peptoid by the addition of an acid, such as formic acid, or trifluoroacetic acid, yielding a terminal carboxylic acid. The excess acid can be removed by rotary evaporation, and the blocks recovered and used for the synthesis of β-peptoid polymers by solid-phase synthesis.

Solid-phase synthesis of the peptoid polymer is achieved by linking the blocks to a solid support through a cleavable linking group via the free carboxylic acid. Suitable supports are described by Bunin, B. A. in "The Combinatorial Index" (Academic Press NY(1998)). The support can, for example, be an inert polymeric material such as polystyrene, which is functionalized with an amine or alcohol group. A linker group such as the "Wang" or "Rink" linker that is specially designed to release the synthesized compound is particularly useful; many of these are well known in the art, and are described by Bunin (supra). Prior to linking the β-peptoid blocks, the solid support can first be reacted with another spacer molecule. This spacer molecule can serve the purpose of ensuring high initial loadings of the resin or can impart useful features in the final β-peptoid, such as providing a site for binding the antimicrobial β-peptoid to an article such as a medical device. In one embodiment of the invention Fmoc-Lysine(Boc) is first loaded onto Rink resin to ensure high initial loadings of the resin. Methods for attaching amino acids to resins are well known in the art and are described in Bodanszky (supra). After the first block is loaded on to the resin, the coupling procedure may be repeated to ensure complete reaction of the solid supported amines. The temporary, beta-amine-protecting group is removed with an appropriate reagent to generate a secondary amine that can be reacted with a second β-peptoid block. In one embodiment of the invention, N-terminal Fmoc groups are used, and are removed by reaction with 20% piperidine/methylene chloride solution. This iterative deprotection/coupling procedure is continued until the desired full-length β-peptoid is synthesized. After the last block is added, the N-terminal amine-protecting group can be removed, if desired.

The N-terminal amine can be left as the secondary amine or, if desired, can be capped with various reagents to impart desired functionality or properties to the final molecule. The β-peptoid can be reacted with acylating agents such as acetic anhydride or acetyl chloride in the presence of triethylamine, or it can be reacted with sulfonyl chlorides such as tosyl chloride to give sulfonamides (see, for example, R. A. Simon, et al (J. Combinatorial Chem., 2005, 7:697) for sulfonation of peptides on a solid support). Alternatively, isocyanates such as phenyl isocyanate can be reacted with the terminal amine in the presence of a suitable base such as triethylamine to generate urea functionality; see, for example, S. Chaterjee, et al (J. Med. Chem., 1997, 40:3820) for the formation of urea on peptides. In one embodiment the solid supported β-peptoid with a free terminal amine is reacted with excess acetic anhydride in triethyl amine and dimethylformamide for 30 minutes to yield the acetamide capped β-peptoid. The β-peptoids can then be cleaved from the linker using standard techniques as described by Bunin (supra). The cleaved β-peptoid may then be purified using, for example, chromatography; mass may be verified by LC-MS.

Method 2

β-Peptoid building blocks may be synthesized by a method according to Hamper, et al. (supra) with modifications. Acryloyl chloride in an inert solvent is added at a temperature of from about 0° C. to about 25° C. to a solid phase synthesis resin, such as Wang resin, which after cleaving from the resin generates a carboxylic acid on the synthesized compound. Other resin types can be used, many of which are described by Bunin (supra). Triethylamine at a ratio of approximately 1:1 to acryloyl chloride is added to the resin, preferably while agitating, to generate acrylate resin after about 1-18 hours. The resin may then be filtered, washed and dried; the coupling procedure may be repeated to ensure complete loading of the resin.

A primary amine is then added to the acrylate resin in a Michael-type reaction to generate a resin-bound aminoester. The primary amine may be selected from R—$NH_2$ or $R_1$—$NH_2$ as described under Method 1 above; protecting groups are added to the amines as necessary. The resin may then be filtered and washed with inert solvents such as methylene chloride, dimethylformamide and methanol. The amine on the resin may then be acrylated by adding acryloyl chloride and a suitable base such as triethylamine to the resin, followed by a second Michael Addition reaction with a primary amine. The iterative acrylation/Michael Addition reactions are repeated until the β-peptoid block of desired composition and length is achieved. The terminal secondary amine functionality is protected with a suitable group such as 9-fluorenylmethoxycarbonyl (FMOC) to give fully protected building blocks, as described above. The β-peptoid block may be cleaved from the resin by treatment with an appropriate reagent and used in the synthesis of full-length β-peptoids. In one embodiment of the invention, Wang polystyrene resin is used and the β-peptoid block is cleaved from the support using a solution of 50% trifluoroacetic acid in dicloromethane. The β-peptoid may then be synthesized and purified using these blocks, as described under Method 1 above.

Applications

β-Peptoids produced by the present invention are effective as antimicrobials and can be employed to kill, inhibit the growth of, or prevent the growth of microorganisms such as Gram-positive bacteria, Gram-negative bacteria, viruses, and fungi. The β-peptoids of the present invention are effective in antimicrobial compositions for use against disease-causing organisms in humans, animals, aquatic and avian species, and plants. The β-peptoids and compositions thereof can also be used as preservatives or sterilants for articles susceptible to microbial contamination. The β-peptoids of the present invention and compositions thereof can be administered to a target cell or host by direct or indirect application. For example, the β-peptoid may be administered topically, systemically or as a coating. The β-peptoids of the present invention and compositions thereof may also be bound to or incorporated into substrates to provide antimicrobial substrates to reduce or inhibit microbial contamination of the substrate. The present invention also provides articles comprising the antimicrobial substrates of the invention.

Substrates suitable for the present invention include conventional polymers selected from the group consisting of latex, polyvinyl chloride, polyimide, polyesters, polyethylene, polypropylene, polyamides, polyacrylates, polyolefins, polysaccharides, polyurethane, polysulfone, polyethersulfone, polycarbonate, fluoropolymers, cellulosics, synthetic rubber, silk, silicone, and mixtures or blends thereof. Additional polymer substrates are also functionalized polymer substrates comprising the aforementioned polymers and that additionally contain, or may be functionalized to contain, active groups with which β-peptoids may react, and which allow for immobilization of the β-peptoids. Examples of active groups include, but are not limited to: acrylic acid, acetal, hydroxyl, amines, epoxides, carboxylates, anhydrides, isocyanates, thioisocyanates, azides, aldehydes, halides, acyl halides, aryl halides and ketones at 1 to 50% by weight of the polymer. Various methods of protein or peptide immobilization are described in Protein Immobilization (Richard F. Taylor (ed.), Marcel Dekker, New York, 1991); similar methods may be used as in known to those skilled in the art for the immobilization of β-peptoids.

Substrates suitable for the present invention also include ceramics, glass, metal, metal oxides, and composites comprised of ceramics, glass, metal or metal oxides plus polymers as described above. Suitable metals include steel, stainless steel, aluminum, copper, titanium, alloys thereof, and combinations thereof.

Additional substrates suitable for the present invention include artificial (or synthetic) marble. Artificial marbles encompass cultured marble, onyx and solid surface materials typically comprising a resin matrix, said resin matrix comprising one or more fillers. Typically, cultured marble is made of a gel coating of unfilled unsaturated polyester on a substrate of a filled unsaturated polyester. The filler may be calcium carbonate or a similar material. Onyx typically consists of a gel coat of unfilled unsaturated polyester on a substrate of filled unsaturated polyester. The filler in this case is typically alumina trihydrate (ATH). Solid surface materials are typically filled resin materials and, unlike cultured marble or onyx, do not have a gel coat. Corian® material available from E. I. du Pont de Nemours and Company (DuPont), Wilmington, Del., is a solid surface material comprising an acrylic matrix filled with ATH. An additional solid surface DuPont material, known by the brand name Zodiaq®, is described as an engineered stone or artificial granite. Such materials are made from an unsaturated polyester matrix filled with quartz.

The articles of the present invention have antimicrobial β-peptoids of the invention bound to or incorporated into a substrate. The use of antimicrobial β-peptoids for rendering substrates antimicrobial provides many advantages to traditional molecules in that β-peptoids exhibit rapid biocidal activity, broad spectrum activity, reduced environmental toxicity and a reduced likelihood of causing organisms to become resistant. β-Peptoids can be bound to a substrate either physicochemically, or covalently. Physicochemical binding of β-peptoids to the substrate may occur by any one or combinations of the following forces: electrostatic, hydrogen bonding, and Van der Waals. Alternatively, β-peptoids may be bound to the substrate surface by a covalent bond. Additionally, antimicrobial β-peptoids of the present invention can be incorporated into the polymer by mixing with the polymer, for example by dissolving the β-peptoid and the polymer in a common solvent and casting or molding the β-peptoid:polymer mixture into an article.

In one embodiment, the antimicrobial β-peptoid is bound to the substrate by coating a substrate polymer with an aqueous or non-aqueous solution of the β-peptoid, wherein the β-peptoid is at concentration ranging from about 0.0001 to about 20 weight percent. The β-peptoid is contacted with the substrate polymer, and the p-peptoid and substrate polymer are optionally shaken at temperatures ranging from about −10° C. to about 150° C. for a period of time ranging from about 0.1 min to about 96 hrs. Preferably the β-peptoid and substrate polymer are shaken at a temperature of from about 25° C. to about 80° C. for a period of time ranging from about 1 min to about 24 hrs.

In another embodiment, the substrate polymer is primed to generate active groups that will bind to the antimicrobial β-peptoid. Surface modification of the polymer may be achieved by a variety of techniques well known in the art including: oxidation, reduction, hydrolysis, plasma, and irradiation. Substrate polymers containing acid or base hydrolyzable groups such as polyesters, polyamides, and polyurethanes may be treated with acid or base first. Subsequently, the hydrolyzed polymer is brought into contact with an aqueous or non-aqueous solution of from about 0.001 to about 20 weight percent of the antimicrobial β-peptoid. The β-peptoid and the polymer may be shaken at temperatures ranging from about −10° C. to about 150° C. for a period of time ranging from about 0.1 min to about 96 hrs. Preferably the β-peptoid and substrate polymer are shaken at a temperature of from about 25° C. to about 80° C. for a period of time ranging from about 10 min to about 24 hrs.

In another embodiment, a commercial substrate polymer containing 1-50% active groups is brought into contact with an aqueous or non-aqueous solution comprising from about 0.0001 to about 20 weight percent of the antimicrobial β-peptoid.

After treatment with the antimicrobial β-peptoid, the article may be washed, preferably with deionized water. Optionally, the article may then be dried via methods known in the art. Such methods include ambient air drying, oven drying, and air forced drying. In one preferred embodiment, the article is dried at about 50° C. to about 120° C., more preferably at about 50° C. to about 100° C., for about 15 min to about 24 hrs.

Articles comprising the polymer substrate of the present invention may be in the form of or comprise an extrudate, film, membrane, laminate, knit fabric, woven fabric, nonwoven fabric, fiber, filament, yarn, pellet, coating, or foam. Articles may be prepared by any means known in the art, such as, but not limited to, methods of injection molding, extruding, blow molding, thermoforming, solution casting, film blowing, knitting, weaving, or spinning.

The preferred articles of the present invention provide multiple uses, since many articles benefit from a reduction in microbial growth and a wide variety of substrates are included in the present invention. The following are examples of articles wherein it is desirable to reduce microbial growth in or on the article in the end-use for which the particular article is commonly used.

The articles of the invention include packaging for food, personal care (health and hygiene) items, and cosmetics. By "packaging" is meant either an entire package or a component of a package. Examples of packaging components include but are not limited to packaging film, liners, absorbent pads for meat packaging, tray/container assemblies, caps, adhesives, lids, and applicators. The package may be in any form appropriate for the particular application, such as a can, box, bottle, jar, bag, cosmetics package, or closed-ended tube. The packaging may be fashioned by any means known in the art, such as by extrusion, coextrusion, thermoforming, injection molding, lamination, or blow molding.

Some specific examples of packaging include, but are not limited to bottles, tips, applicators, and caps for prescription and non-prescription capsules and pills; solutions, creams, lotions, powders, shampoos, conditioners, deodorants, antiperspirants, and suspensions for eye, ear, nose, throat, vaginal, urinary tract, rectal, skin, and hair contact; lip product packaging, and caps.

Examples of applicators include those for lipstick, chapstick, and gloss; packages and applicators for eye cosmetics, such as mascara, eyeliner, shadow, dusting powder, bath powder, blusher, foundation and creams. These applicators are used to apply substances onto the various surfaces of the body and reduction of bacterial growth will be beneficial in such applications.

Other forms of packaging components included in the present invention include drink bottle necks, replaceable caps, non-replaceable caps, and dispensing systems; food and beverage delivery systems; baby bottle nipples and caps; and pacifiers. Where a liquid, solution or suspension is to be applied, the package may be fashioned for application in a form for dispensing discrete drops or for spraying of droplets. The invention will also find use in pharmaceutical applications fashioned as inhalers.

Examples of end-use applications, other than packaging, in the area of food handling and processing that benefit from antimicrobial functionality and wherein microbial growth is reduced in the particular end-use of the consumer are coatings for components of food handling and processing equipment, such as temporary or permanent food preparation surfaces; conveyer belt assemblies and their components; equipment for mixing, grinding, crushing, rolling, pelletizing, and extruding and components thereof; heat exchangers and their components; and machines for food cutting and slicing and components thereof. Where the surface of such equipment components is metal, the metal could be coated directly, or a coating of a polymer or functionalized polymer could first be applied to the metal surface. Alternatively, a film of such a polymer or functionalized polymer could be coated with an antimicrobial β-peptoid of the invention and then applied to the equipment surface. Additional articles of the invention include foods and seeds.

Articles of the present invention can also be used in or as items of apparel, such as a swimsuit, undergarment, shoe component (for example, a woven or nonwoven shoe liner or insert), protective sports pad, child's garment. Articles of the invention also include protective medical garments or barrier materials, such as gowns, masks, gloves, slippers, booties, head coverings or drapes.

Articles of the present invention can also be used in or as medical materials, devices, or implants, such as bandages, adhesives, gauze strips, gauze pads, syringe holders, catheters such as peripheral IV catheters and central venus catheters comprised of either polyurethane or silicon, sutures, urinary catheter ostomy ports, orthopedic fixtures, orthopedic pins, pacemaker leads, defibrillator leads, ear canal shunts, vascular stents, cosmetic implants, ENT implants, staples, implantable pumps, hernia patches, plates, screws, blood bags, external blood pumps, fluid administration systems, heart-lung machines, dialysis equipment, artificial skin, artificial hearts, ventricular assist devices, hearing aids, vascular grafts, pacemaker components, hip implants, knee implants, and dental implants.

In the hygiene area, articles of the present invention include personal hygiene garments such as diapers, incontinence pads, sanitary napkins, sports pads, tampons and their applicators; and health care materials such as antimicrobial wipes, baby wipes, personal cleansing wipes, cosmetic wipes, diapers, medicated wipes or pads (for example, medicated wipes or pads that contain an antibiotic, a medication to treat acne, a medication to treat hemorrhoids, an anti-itch medication, an anti-inflammatory medication, or an antiseptic).

Articles of the present invention also include items intended for oral contact, such as a baby bottle nipple, pacifier, orthodontic appliance or elastic bands for same, denture material, cup, drinking glass, toothbrush, or teething toy.

Additional child-oriented articles that benefit from the present invention include baby bottles, baby books, plastic scissors, toys, diaper pails, and a container to hold cleansing wipes.

Household articles of the present invention include telephones and cellular phones; fiberfill, bedding, bed linens, window treatments, carpet, flooring components, foam padding such as mat and rug backings, upholstery components (including foam padding), nonwoven dryer sheets, laundry softener containing sheets, automotive wipes, household cleaning wipes, counter wipes, shower curtains, shower curtain liners, towels, washcloths, dust cloths, mops, table cloths, walls, and counter surfaces.

The current invention is also useful in reducing or preventing biofilm growth on the surface of separation membranes (for example, pervaporation, dialysis, reverse osmosis, ultrafiltration, and microfiltration membranes) comprised of polymer substrates of the invention.

In order to impart antimicrobial functionality to the products listed, the product can be treated with an antimicrobial β-peptoid oligomer of the invention before it is manufactured, or after, or at any time during manufacture of the product. For example, in making an antimicrobial shower curtain, an antimicrobial β-peptoid oligomer of the invention may be bound to or incorporated into the polymer substrate, followed by fashioning a shower curtain from the treated material. Alternatively, treatment of the polymer substrate with an antimicrobial β-peptoid oligomer of the invention may be performed after the substrate is made into a shower curtain.

Antimicrobial substrates or articles prepared by methods of the invention exhibit antimicrobial functionality, wherein microbes are killed, or microbial growth is reduced or prevented. Antimicrobial activity of the antimcrobial substrate or article can be determined by using any of a number of methods well known in the art, such as the Shake Flask Test described in Examples 33-54 of the present invention. Additional methods for determining antimicrobial activity are discussed in Tenover et al. (eds.), Manual of Clinical Microbiology, 7$^{th}$ Edition, Section VIII, 1999, American Society for Microbiology, Washington, D.C.

The present invention provides a method for killing, inhibiting, or preventing the growth of at least one microbe, the method comprising contacting the microbe with an effective amount of an antimicrobial β-peptoid oligomer according to Formula (I).

The present invention also provides antimicrobial compositions comprising at least one antimicrobial β-peptoid oligomer, wherein the β-peptoid oligomer is represented by Formula (I).

The antimicrobial β-peptoid of Formula (I) comprises from about 0.00001% to about 20% by weight of the composition. In another embodiment of the invention the antimicrobial β-peptoid comprises from about 0.0001% to about 10% by weight of the composition. In still another embodiment of the invention the antimicrobial β-peptoid comprises from about 0.001% to about 5% by weight of the composition.

The present invention also comprises methods for killing, inhibiting, or preventing the growth of at least one microbe, the method comprising administering an effective amount of an antimicrobial composition comprising at least one antimicrobial β-peptoid wherein said antimicrobial β-peptoid is represented by Formula (I).

The present invention also comprises methods for killing, inhibiting, or preventing the growth of at least one microbe, the method comprising bringing at least one microbe into contact with a substrate coated with an effective amount of at least one antimicrobial β-peptoid selected from β-peptoids of Formula (I).

The present invention is further described in, but not limited by, the following specific embodiments. Examples 54 through 59 are prophetic Examples.

GENERAL METHODS AND MATERIALS

Synthesis reagents were obtained from Aldrich Chemical Co. (Milwaukee, Wis.). Unprotected and protected amino acids and 1-hydroxybenzotriazole (HOBt) were obtained from Applied Biosystems (Foster City, Calif.). Wang polystyrene resin was obtained from Novabiochem ro Argonaut Technologies foster City, Calif.; Rink resin was obtained from Novabiochem or Argonaut Technologies Foster City, Calif.

The meaning of abbreviations is as follows: "L" is liter, "ml" is milliliter, "µl" is microliter, "mmol" is millimole, "M" is molar, "hr(s)" is hour(s), "min(s)" is minute(s), "LC-MS" is liquid chromatography-mass spectrometry, "mm" is millimeter, "° C." is degrees Centigrade, "Prep-HPLC" is preparatory high pressure liquid chromatography, "g" is gram.

Synthesis of β-peptoids:

All solid phase syntheses were carried out in Quest 205 (larger scale) or Quest 210 (smaller scale) synthesizers (Argonaut Technologies).

Figure 2A:
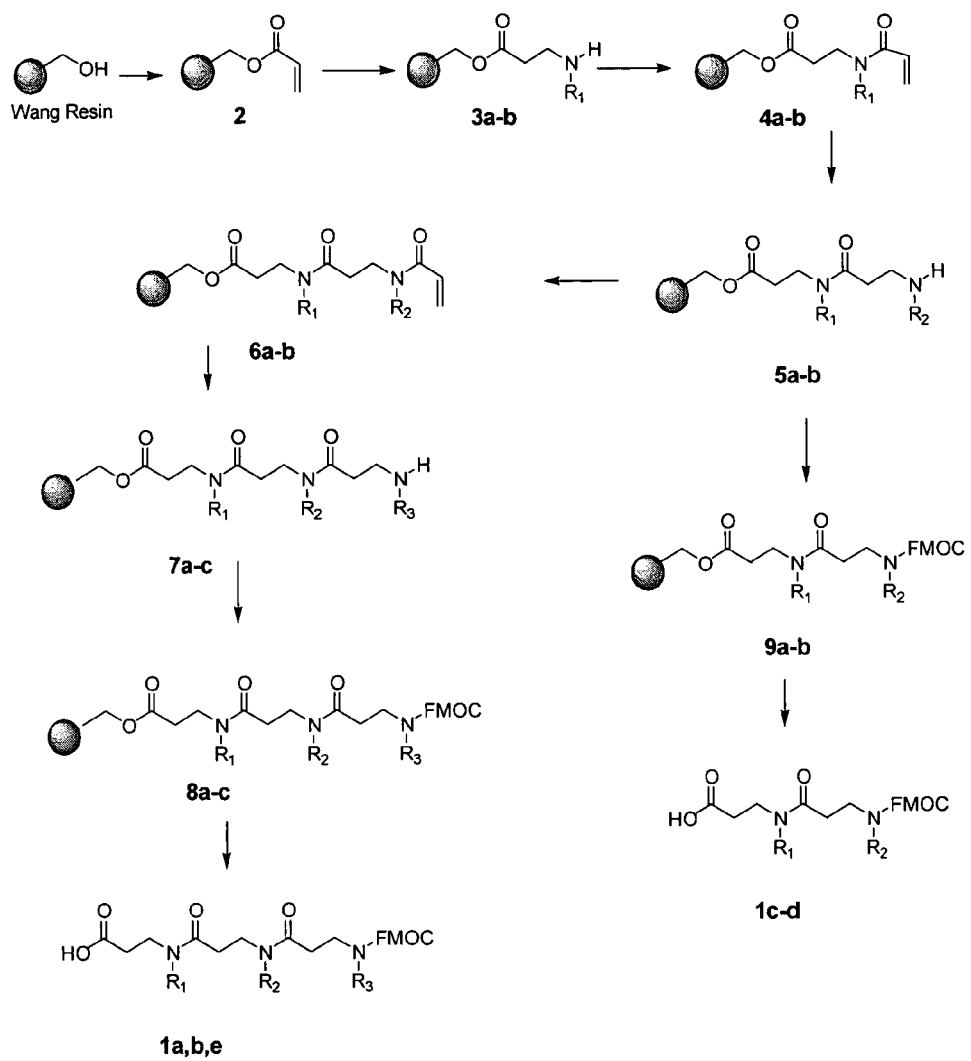
FIG. 2A shows the general scheme for the synthesis.
Figure 2B:
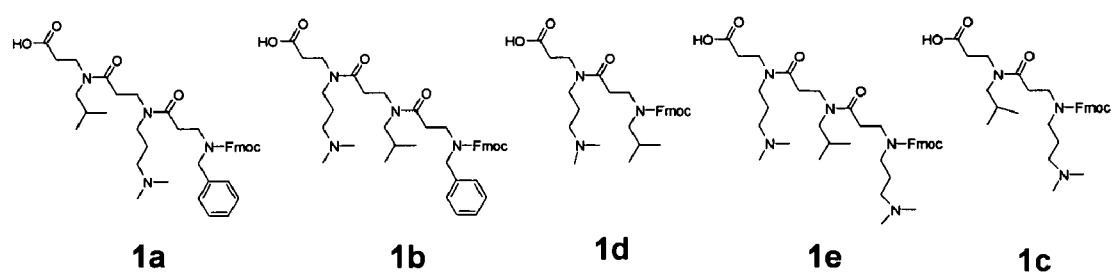
FIG. 2B shows the structure of the β-peptoid blocks that were synthesized using this method.

FIGS. 1 and 2 show the general synthesis scheme for the β-peptoid blocks, as well as the structure of the β-peptoid blocks synthesized.

General Synthesis Methods:

Method "A": Loading of Acryloyl Chloride onto Wang Polystyrene Resin

Wang polystyrene resin was added to a 50 ml reaction vessel. A solution of acryloyl chloride in 20 ml tetrahydrofuran was added to the resin. While agitating, triethylamine was slowly added. After 20 hrs the resin was filtered and washed with dimethylformamide: methanol: tetrahydrofuran (DMF:MeOH:THF) twice for each solvent and then dried under a stream of dry nitrogen. The coupling procedure was repeated to ensure complete loading of the resin. Resin (100 mg) was removed and dried under high vacuum for 1 hr. The resin was mixed with 1.0 ml of 10.5 mmol hexamethyldisiloxane in 1:1 trifluoroacetic acid (TFA):deuterated chloroform for 15 min. The loading of the resin was determined using the method of Hamper, et al. (J. Org. Chem. (1998) 63:708). Acetic anhydride:triethylamine: DMF (1:1:2, 25 ml) was added to the dry resin and the mixture was agitated for 1 hr to cap the resin. The resin was filtered and washed with DMF:MeOH:THF twice for each solvent; the resin was then dried under a stream of dry nitrogen.

Method "B": Michael Addition

A primary amine in 20 ml dimethylsulfoxide (DMSO) was added to the reaction vessel containing acrylated Wang polystyrene resin (synthesized according to Method A) and the mixture was agitated and heated to 50° C. for 48 hrs. The resin was filtered and washed with DMF:MeOH:THF twice for each solvent and the resin was then dried under a nitrogen stream.

Method "C": Acrylation of an Amine on Wang Polystyrene Resin

A solution of acryloyl chloride in 20 ml of tetrahydrofuran was added to the reaction vessel containing an amine bound to Wang polystyrene resin (from Method B). Triethylamine was added while agitating the resin slurry. After mixing for 20 hrs, the resin was filtered and washed with DMF:MeOH: THF twice for each solvent and the resin was then dried under a nitrogen stream. The addition of acryloyl chloride was repeated to ensure complete reaction of the amine groups.

Method "D": FMOC Protection of Resin-Bound Peptoid Blocks

9-Fluorenylmethylchloroformate in 20 ml N-methyl pyrrolidone (NMP) was added to the reaction vessel containing Wang polystyrene resin-bound peptoid block (from example 7a). Diisopropylethylamine was added portionwise while mixing and agitated for 1.0 hr. The resin was drained and washed with NMP:DMF:MeOH:DCM twice for each solvent and the resin was then dried under a stream of dry nitrogen.

Method "E": Cleavage of Protected Peptoid Blocks from the Resin

TFA:DCM (1:1, 30 ml) was added to the resin containing the protected β-peptoid block (from 8a). The slurry was agitated at 25° C. for 1.0 hr, and then filtered and concentrated under vacuum. The crude β-peptoid was purified by Prep-HPLC (Gilson HPLC, MetaChem Polaris C18-A 10 μm 212×150 mm column, $CH_3CN$ 0.05M TFA:$H_2O$ 0.05M TFA with a gradient from 95:5-0:100 over 25.0 min). Product fractions were combined and concentrated under vacuum. Sample was then redissolved in 10 ml of 0.1 M HCl and lyophilized, repeating the lyophilization 3 times. Final product samples of building blocks were analyzed by LC-MS. The samples were run on a Micromass LCT time of flight mass spectrometer equipped with the Lockspray source option in Electrospray positive ionization mode. The instrument was scanned from 100 to 1600 Daltons in 0.9 seconds with a 0.1 second interscan delay for 40 minutes. The LC used was a Waters Alliance HT 2790 with an Agilent Zorbax SB-C18 2.1×150 mm reverse phase column. Solvent A was 1% acetonitrile in $H_2O$ with 0.1% formic acid and Solvent B was 100% acetonitrile with 0.1% formic acid. The gradient used is described below:

| Time | Solvent B |
|---|---|
| 0.0 | 10% |
| 30 | 100% |
| 40 | 100% |
| 42 | 10% |
| 51 | 10% |

In all cases 5 μl of solution was injected and both the sample and reserpine reference spectra were acquired to provide accurate mass elemental composition information.

Method "F": Michael Addition of Amines to Acrylamides and Acrylates—Synthesis of Compound 10a Mono-(benzyloxylcarbonyl (CBZ) protected ethylene diamine (12.21 g, 63.2 mmol) and MeOH (55 ml) were added to a 200 ml round bottom flask. To this solution was added 4.63 ml t-butylacrylate, and the resulting solution was heated to 60° C. for 48 h. The reaction mixture was cooled to room temperature and the solvent was removed by rotary evaporation. The resulting oil was suspended in 60 ml THF and left in the refrigerator overnight. The white precipitate (starting amine) which formed was filtered off and the filtrate concentrated to about 15 ml; the filtrate was allowed to precipitate a second time and the white precipitate was removed by filtration. The filtrate containing the desired product and some starting amine was then evaporated to give 15.0 g of a clear oil which was suitable for use in the next step.

Method "G": Addition of Acryloyl Chloride to Substituted 3 Amino Propionic Acids—Synthesis of Compound 11a Compound 10a (9.5 g, 29.5 mmol) was charged to a 100 ml flask along with 35 ml of dry THF. The solution was cooled to 0° C. and 6.7 ml (48 mmol) triethylamine and a catalytic amount of dimethylaminopyridine (DMAP) was added. Acryloyl chloride (3.08 ml, 38 mmol) was then added dropwise through a syringe so that the temperature remained below 5° C. After the addition was complete, the reaction mixture was stirred at 0° C. for 30 min, and then at room temperature for 4 h. The THF was removed by rotary evaporation to give a gummy solid. The solid residue was dissolved in ethyl acetate (EtOAc) and washed first with 1N HCl, followed by 5% $NaHCO_3$, and then saturated NaCl. The solution was dried over sodium sulfate and then the solvent was removed in vacuo to give 11.7 g of oil. The compound was purified by flash chromatography eluting with 60:40 Hexanes:EtOAc. The yield was 4.98 g.

Method "H": FMOC Protection of β-Peptoid Blocks—Synthesis of Compound 15a

A solution of Compound 14a (2.6 g, 4.54 mmol) in 4 ml THF was added dropwise to a solution of 4 ml water and 1.48 g (13.99 mmol) sodium carbonate at 0° C. To this mixture was added in one portion 1.298 g (5.0 mmol) fluorenylmethylchloroformate and the temperature kept first at 5° C. for 45 min, and then at 25° C. for 30 min. The THF was removed on the rotary evaporator and the resulting residue was diluted in 75 ml water and extracted with EtOAc. The organic extracts were washed with brine and dried over sodium sulfate. After removal of the solvent (EtOAc), column chromatography using 70:30 Hexane:EtOAc gave the desired compound (yield, 4.51 g; LC-MS (m/z) 799.4).

Method "I": Removal of t-Butyl Protecting Groups from Peptoid Blocks—Synthesis of Compound 1f Formic acid (20 ml) and Compound 15a (4.51 g) were added to a 100 ml flask. The mixture was stirred for 3 h at 50° C. The reaction mixture was cooled to 25° C. and the formic acid was removed by rotary evaporation. The residue was dissolved in EtOAc and washed with water, then dried over sodium sulfate. The solvent was removed and the compound dried under high vacuum to give Compound 1f (yield, 4.2 g).

Method "J": Loading FMOC-Lys(BOC)-OH onto Rink Resin

A reaction vessel containing 2.0 g Rink resin (1.92 mmol) was treated with 25 ml of 25% piperidine/THF for 1.0 hr. The resin was drained and washed with DMF:MeOH:THF twice for each solvent, and dried under $N_2$ pressure. A solution of 9-fluorenylmethoxycarbonyl (FMOC)-Lys (BOC)—OH (7.68 mmol) and HOBt (7.68 mmol) in 30.0 ml NMP was added to the resin. Diisopropylcarbodiimide (7.68 mmol) was added and the mixture was agitated for 18 hrs under $N_2$. The resin was drained and washed with DMF:MeOH:DCM twice for each solvent and dried under $N_2$ pressure. Dry resin (10 mg) was removed and the loading was measured by FMOC quantitation. Acetic anhydride:triethylamine:DMF (1:1:2, 25.0 ml) was added to the dry resin and the mixture was agitated for 1 hr to cap the resin. The resin was filtered and washed with DMF:MeOH:THF twice for each solvent and dried under nitrogen pressure.

Method "K": Coupling Cycle Procedure

The reaction vessel containing Rink-FMOC-Lys(BOC)-OH resin (0.02 mmol) was treated with 3.0 ml of 25% piperidine/THF for 1.0 hr. The resin was drained and washed with DMF:MeOH:THF twice for each solvent, and dried under $N_2$ pressure. Compound 1a (0.08 mmol) was added to the resin as a 0.5 mg/ul stock in NMP and diisoproylethylamine (DIEA) (0.1 mmol). O-(7-Azabenzotriazol-1-yl)-N,N,N',N'-tetramethyluronium hexafluorophosphate (HATU) (0.08 mmol) in 1.0 ml NMP was added to the resin and the mixture was agitated at 25° C. for 20 hrs under $N_2$. The resin was drained and washed with DMF:MeOH:THF twice for each solvent, and dried under $N_2$ pressure. Dry resin (10 mg) was removed and the loading was determined by FMOC quantitation. In addition, reaction completion was checked by cleaving a small sample as follows: resin (5.0 mg) was removed and cleaved with 1.0 ml of 50% TFA/DCM for 30 min. The resin was filtered and washed with DCM. The solvent was evaporated and the residue was dissolved in 1.0 ml of $CH_3CN$. The reaction was determined to be complete by LC-MS (Agilent 1100 LC-MSD, API-ES+, Agilent Eclipse XDB-C18 2.1×50 mm, $CH_3CN$ 0.05 M TFA:$H_2O$ 0.05 M TFA 95:5-0:100, 4.50 min). Acetic anhydride:triethylamine:DMF (1:1:2, 3.0 ml) was added to the dry resin and the mixture was agitated for 1 hr to cap the resin. This capping step was only performed for the first coupling cycle to ensure high initial loadings of the resin. The resin was filtered and washed with DMF:MeOH:THF twice for each solvent and dried under nitrogen pressure.

Method "L": Acylation Procedure

The vessel containing the resin bound, fully formed, Fmoc deprotected β-peptoid (See for instance, example 11) was treated with 3.0 ml of a 2:1:1 solution of DMF:acetic anhydride: triethylamine for 1 h at room temperature. After 1 h, the vessel was drained and its contents washed twice with DMF, twice with methanol and twice with dichloromethane. The resin was then dried under a stream of nitrogen.

Method "M": Cleavage Procedure

The β-peptoids were cleaved from the solid support by treatment with 3 ml of a 50% TFA/dichloromethane solution for 30 min at room temperature. The mixture was filtered and the resin was washed three times with dichloromethane. The filtrates were combined and concentrated in vacuo to give the crude products. The side chain CBZ protecting groups, if any, were removed by hydrogenation of a methanolic solution over 5% Paladium on carbon (Aldrich Chemical). The crude peptoid was purified by Prep-HPLC (Gilson HPLC, MetaChem Polaris C18-A 10 μm 212×150 mm column, $CH_3CN$ 0.05M TFA:$H_2O$ 0.05M TFA 95:5-0:100, over 25.0 min). Product fractions were combined and concentrated under vacuum. Sample was then redissolved in 10 ml of 0.1 M HCl and lyophilized, repeating the lyophilization 3 times. Final product peptoids were analyzed by LC-MS. The samples were run on a Micromass LCT time of flight mass spectrometer equipped with the Lockspray source option in electrospray positive ionization mode. The instrument was scanned from 100 to 1600 daltons in 0.9 seconds with a 0.1 second interscan delay for 40 minutes. The LC used was a Waters Alliance HT 2790 with an Agilent Zorbax SB-C18 2.1×150 mm reverse phase LC column. Solvent A was 1% acetonitrile in $H_2O$ with 0.1% formic acid and Sovent B was 100% acetonitrile with 0.1% formic acid. The gradient used is described below:

| Time | Solvent B |
|---|---|
| 0.0 | 10% |
| 30 | 100% |
| 40 | 100% |

-continued

| Time | Solvent B |
|---|---|
| 42 | 10% |
| 51 | 10% |

In all cases 5 μl of solution was injected and both the sample and reserpine reference spectra were acquired to provide accurate mass elemental composition information.

Synthesis of 2-(Amino-ethyl)-Benzylcarbamate (Compound 17) Ethylene diamine (78.3 ml, 1.172 mol ) and 300 ml of dry methylene chloride were mixed in a 1 L flask under $N_2$. The mixture was cooled to 0° C. and a solution of benzyloxychloroformate (16.74 ml, 0.117 mol) in 85 ml methylene chloride was added dropwise. The mixture was kept at 0° C. for 1 h after the addition was complete and then stirred at 25° C. overnight. The reaction mixture was washed in a separatory funnel with 1 N HCl until the aqueous layer was acidic to litmus. The acidified aqueous layers were then extracted three times with methylene chloride, and the combined organic layers were dried over sodium sulfate. The solvent was removed to give 18.04 g of a clear oil.

3-(Hydroxy-propyl)-Carbamic Acid Benzyl Ester (Compound 18) 4-Amino-1-butanol (15.0 g, 0.168 mmol) was added to DIEA (29.0 g, 0.252 mmol) in 150 ml anhydrous DCM and cooled to 0° C. in an ice bath under $N_2$. A solution of benzylchloroformate (34.45 g, 0.202 mmol) in 30.0 ml anhydrous DCM was added with stirring. After complete addition the mixture was stirred in the ice bath for 30 min, followed by warming to room temperature and continued stirring overnight. The mixture was extracted from water twice, washed with 0.5 M HCl, washed with brine, and then dried with $MgSO_4$. White crystals formed in the DCM filtrate immediately. A small amount of DCM was added to get the solid free flowing, followed by chilling at 0° C. for 20 min. The white crystals that formed were filtered off. Addition of more DCM followed by chilling was repeated to obtain additional product. The solid was dried in a dessicator under high vacuum overnight (yield, 31.08 g (83%)).

(4-Amino-butyl)-Carbamic Acid Benzyl Ester (Compound 19) 3-(Hydroxy-propyl)-carbamic acid benzyl ester (5.0 g, 1.0 mmol), di-tert-butyl-iminodicarbonate (5.45 g, 1.05 mmol) and triphenylphosphine (7.83 g, 1.25 mmol) in 100 ml anhydrous THF was cooled to ° C. in a dry ice/acetone bath. Diethylazodicarboxylate (Aldrich chemical Co.) (5.53 g, 1.33 mmol) in 20 ml anhydrous THF was added dropwise with vigorous stirring, keeping the temperature at 0° C. After complete addition the mixture was stirred at 0° C. for 30 min, followed by allowing the mixture to come up to room temperature and stirring for 2 hrs. The solution was concentrated in vacuo to an oil. The product was purified on silica gel with 2:8 EtOAc:Hexanes. The reaction yielded 5.1 g of the di-boc protected amine. The Boc groups were cleaved with 1.0 M HCl in diethylether to yield 2.68 g (50%) of Compound 19.

EXAMPLE 1

Synthesis of Compound 1a

Synthesis of resin bound acrylic acid 2: Method "A" was followed with Wang polystyrene resin (3.0 g, 2.67 mmol). Acryloyl chloride (1.71 g, 5.34 mmol) and triethylamine (1.96 g, 8.01 mmol) were added to the resin. Resin (94.8 mg) was removed and the loading was determined to be 0.902 mmol/g. The resin was dried under a stream of dry nitrogen.

Synthesis of 3a: The reaction vessel containing Compound 2 (3.0 g, 2.67 mmol) was treated by Method "B" with isobutylamine (1.95 g, 26.7 mmol).

Synthesis of 4a: The reaction vessel containing Compound 3a was treated by Method "C" with acryloyl chloride (1.71 g, 5.34 mmol) and triethylamine (1.96 g, 8.01 mmol).

Synthesis of 5a: The reaction vessel containing Compound 4a was treated by Method "B" with dimethylaminopropylamine (2.728 g, 26.7 mmol).

Synthesis of 6a: The reaction vessel containing Compound 5a was treated by Method "C" with acryloyl chloride (1.71 g, 5.34 mmol) and triethylamine (1.96 g, 8.01 mmol).

Synthesis of 7a: The reaction vessel containing Compound 6a was treated by Method "B" with benzylamine (2.86 g, 26.7 mmol).

Synthesis of 8a: The reaction vessel containing Compound 7a was treated by Method "D" with FMOC—Cl (2.07 g, 8.01 mmol) and DIEA (2.07 g, 16.02 mmol).

Synthesis of 1a: Using method "E" with 30 ml TFA/DCM Compound 8a was cleaved from the resin and collected. The crude product was purified by Prep-HPLC. The product peak eluted between 15.5 and 18.5 min. The product identity was verified by LC-MS analysis, with the product peak eluting at 10.00 min. The yield after salt exchange was 177 mg of pure 1a.

EXAMPLE 2

Synthesis of Compound 1b

Resin bound acrylic acid 2: Method "A" was followed with NovaSyn® TG-HMP resin (40.0 g, 10.8 mmol; EMD Biosciences, San Diego, Calif.). Acryloyl chloride (1.95 g, 21.6 mmol) and triethylamine (3.28 g, 32.4 mmol) were added to the resin. Resin (121.2 mg) was removed and the loading was determined to be 0.188 mmol/g. The resin was capped and dried under a dry nitrogen stream.

Synthesis of 3b: The reaction vessel containing Compound 2 (6.0 g, 1.2 mmol) was treated by Method "B" with dimethylaminopropylamine (1.23 g, 12.0 mmol). The reaction was shown to be complete by LC-MS, with the product peak eluting at 0.107 min.

Synthesis of 4b: The reaction vessel containing Compound 3b was treated by Method "C" with acryloyl chloride (0.291 g, 2.4 mmol) and triethylamine (0.492 g, 3.6 mmol). The reaction was shown to be complete by LC-MS, with the product peak eluting at 0.119 min.

Synthesis of 5b: Method "B" was followed; the reaction vessel containing Compound 4b was treated with isobutylamine (0.877 g, 12.0 mmol). The reaction was shown to be complete by LC-MS, with the product peak eluting at 0.115 min.

Synthesis of 6b: The reaction vessel containing Compound 5b was treated by Method "C" with acryloyl chloride (0.291 g, 2.4 mmol) and triethylamine (0.492 g, 3.6 mmol). The reaction was shown to be complete by LC-MS, with the product peak eluting at 1.392 min.

Synthesis of 7b: Method "B" was followed; the reaction vessel containing Compound 6b was treated with benzylamine (1.29 g, 12.0 mmol). The reaction was shown to be complete by LC-MS, with the product peak eluting at 1.562 min.

Synthesis of 8b: The reaction vessel containing Compound 7b was treated by Method "D" with FMOC—Cl (3.49 g, 13.5 mmol) and DIEA (3.49 g, 27.0 mmol).

Synthesis of 1b: The reaction vessel containing Compound 8b was treated with 30 ml of TFA solution. The crude product was purified by Prep-HPLC. The product peak eluted between 12.0 and 14.0 min. Product was verified by LC-MS analysis, with the product peak eluting at 10.00 min. Salt exchange yield pure 1b.

EXAMPLE 3

Synthesis of Compound 1c

Resin bound acrylic acid 2: Method "A" was followed with Wang polystyrene resin (4.0 g, 3.56 mmol). Acryloyl chloride (0.64 g, 7.12 mmol) and triethylamine (1.08 g, 10.68 mmol) were added to the resin. Resin (88.8 mg) was removed and the loading was determined to be 0.844 mmol/g. The resin was capped and dried under a stream of dry nitrogen.

Synthesis of 3a: The reaction vessel containing Compound 2 (4.0 g, 3.56 mmol) was treated by Method "B" with isobutylamine (2.60 g, 35.6 mmol).

Synthesis of 4a: The reaction vessel containing Compound 3a was treated by Method "C" with acryloyl chloride (0.64 g, 7.12 mmol) and triethylamine (1.08 g, 10.68 mmol).

Synthesis of 5a: The vessel containing Compound 4a was treated according to Method "B" with dimethylaminopropylamine (3.63 g, 35.6 mmol).

Synthesis of 9c: The reaction vessel containing Compound 5a was treated by Method "D" with FMOC—Cl (2.76 g, 10.68 mmol) and DIEA (1.43 g, 11.03 mmol).

Synthesis of 1c: The vessel containing Compound 9a was treated by Method "E". The crude. product was purified by Prep-HPLC. The product peak eluted between 12.4 and 13.8 min. The yield after salt exchange was 350 mg of pure 1c.

EXAMPLE 4

Synthesis of Compound 1d

Resin bound acrylic acid 2: Method "A" was followed with Wang polystyrene resin (4.0 g, 3.56 mmol). Acryloyl chloride (0.64 g, 7.12 mmol) and triethylamine (1.08 g, 10.68 mmol) were added to the resin. Resin (96.9 mg) was removed and the loading was determined to be 0.901 mmol/g. The resin was capped and dried under a dry nitrogen stream.

Synthesis of 3b: The reaction vessel containing Compound 2 (4.0 g, 3.56 mmol) was treated by Method "B" with N,N-dimethylaminopropylamine (3.63 g, 35.6 mmol).

Synthesis of 4b: The reaction vessel containing Compound 3b was treated by Method "C" with acryloyl chloride (0.64 g, 7.12 mmol) and triethylamine (1.08 g, 10.68 mmol).

Synthesis of 5b: The reaction vessel containing Compound 4b was treated according to Method "B" with isobutylamine (2.60 g, 35.6 mmol).

Synthesis of 9b: The reaction vessel containing Compound 5b was treated by Method "D" with FMOC-Cl (2.76 g, 10.68 mmol) and DIEA (1.43 g, 11.03 mmol).

Synthesis of 1d: The reaction vessel containing Compound 9b was treated according to Method "E". The crude product was purified by Prep-HPLC. The product peak eluted between 11.1 and 13.5 min. Product was verified by LC-MS analysis, with the product peak eluting at 15.63 min. The yield after salt exchange was 835 mg of pure 1d.

EXAMPLE 5

Synthesis of Compound 1e

Resin bound acrylic acid 2: Method "A" was followed with Wang polystyrene resin (3.0 g, 2.67 mmol). Acryloyl chloride (1.71 g, 5.34 mmol) and triethylamine (1.96 g, 8.01 mmol) were added to the resin. Resin (89.0 mg) was removed and the loading was determined to be 0.932 mmol/g. The resin was capped and dried under a stream of dry nitrogen.

Synthesis of 3b: The reaction vessel containing Compound 2 (3.0 g, 2.67 mmol) was treated by Method "B" with dimethylaminopropylamine (2.728 g, 26.7 mmol).

Synthesis of 4b: The reaction vessel containing Compound 3b was treated by Method "C" with acryloyl chloride (1.17 g, 5.34 mmol) and triethylamine (1.96 g, 8.01 mmol).

Synthesis of 5b: The reaction vessel containing Compound 4b was treated according to Method "B" using isobutylamine (1.95 g, 26.7 mmol).

Synthesis of 6b: The reaction vessel containing Compound 5b was treated by Method "C" with acryloyl chloride (1.17 g, 5.34 mmol) and triethylamine (1.96 g, 8.01 mmol).

Synthesis of 7c: The reaction vessel containing Compound 6b was treated according to Method "B" using dimethylaminopropylamine (2.728 g, 26.7 mmol).

Synthesis of 8c: The reaction vessel containing Compound 7c was treated by Method "D" with FMOC-Cl (2.07 g, 8.01 mmol) and DIEA (2.07 g, 16.02 mmol).

Synthesis of 1e: The vessel containing Compound 8c was treated according to Method "E". The crude product was purified by Prep-HPLC. The product peak eluted between 10.5 and 11.75 min. Product was verified by LC-MS analysis, with the product peak eluting at 10.00 min. The yield after salt exchange was 300 mg of pure 1e.

EXAMPLE 6

Synthesis of Compound 1f

Synthesis of 10a: Mono-CBZ protected ethylene diamine (12.21 g, 63.2 mmol) and 55 ml MeOH were added to a 200 ml round bottom flask. To this solution was added 4.63 ml t-butylacrylate, and the resulting solution was heated to 60° C. for 48 h. The reaction mixture was cooled to room temperature and the solvent was removed by rotary evaporation. The resulting oil was suspended in 60 ml THF and left in the refrigerator overnight. The white precipitate (starting amine) which formed was filtered off and the filtrate was concentrated to about 15 ml; the filtrate was allowed to precipitate a second time and the solids were removed by filtration. The filtrate containing the desired product and some starting amine was then evaporated to give 15.0 g of a clear oil which was suitable for use in the next step.

Synthesis of 11a: To a 100 mL flask was added 9.5 g (29.5 mmol) of Compound 10a along with 35 ml of dry THF. The solution was cooled to 0° C. and 6.7 ml (48 mmol) triethylamine, along with a catalytic amount of DMAP, was added. Acryloyl chloride, 3.08 ml (38 mmol) was then added dropwise through a syringe so that the temperature remained below 5° C. After the addition was complete the reaction mixture was stirred at 0° C. for 30 min, and then at room temperature for 4 h. The THF was removed by rotary evaporation to give a gummy solid. The solid residue was dissolved in EtOAc and washed with 1N HCl, 5% NaHCO$_3$, and saturated NaCl, the residue was then dried and the solvent was removed to give 11.7 g of oil. The compound was purified by flash chromatography, eluting with 60:40 Hexanes:EtOAc (yield 4.98 g).

Synthesis of 12a: Method "F" was used with 8.74 g (23.24 mmol) of Compound 11a, 16.97 ml (232 mmol) isobutylamine, and 50 ml acetonitrile to give 10.43 g of the desired crude product as an oil. The material was suitable for use in the next step.

Synthesis of 13a: Using method "G", 5.0 g (11.1 mmol) of the intermediate 12a, 1.21 g (13.36 mmol) of acryloyl chloride, and 2.33 ml of triethylamine yielded 3.6 g of 13a after purification by flash chromatography.

Synthesis of 14a: General method "F" was used with 3.2 g (6.36 mmol) of Compound 13a, and 4.65 g (63.6 mmol) isobutylamine. The yield was 3.6 g of material suitable for use in the next step.

Synthesis of 15a: A solution of Compound 14a (2.6 g, 4.54 mmol) in 4 ml of THF was added dropwise to a solution of 4 ml water and 1.48 g (13.99 mmol) sodium carbonate at 0° C. To this mixture was added in one portion 1.298 g (5.0 mmol) fluorenylmethylchloroformate; the temperature was maintained at 5° C. for 45 min, and then at 25° C. for 30 min. The THF was removed on the rotary evaporator; the resulting residue was diluted in 75 ml of water and extracted with EtOAc. The organic extracts were washed with brine and dried over sodium sulfate. After removal of the solvent, column chromatography using 70:30 Hexane:EtOAc gave the desired compound (4.51 g; LC-MS (m/z) 799.4).

Synthesis of 1f: Compound 15a (4.51 g) and formic acid (20 ml) were added to a 100 ml flask. The mixture was stirred for 3 h at 50° C. The reaction mixture was cooled to 25° C. and the formic acid was removed by rotary evaporation. The residue was dissolved in EtOAc, washed with water, and then dried over sodium sulfate. The solvent was removed and the compound was dried under high vacuum to give compound if (4.2 g).

EXAMPLE 7

Synthesis of Compound 1g

Synthesis of 12b: Method "F" was used with Compound 11a (1.0 g, 2.67 mmol) and 2.59 g (13.33 mmol) of mono-CBZ protected ethylene diamine. The yield was 3.1 g of a mixture of the desired Michael intermediate and excess mono-CBZ protected ethylene diamine.

Synthesis of 13b: Method "G" was used with 3.1 g (5.448 mmol) of Compound 12b, 0.64 g (7.08 mmol) acryloyl chloride, and 0.9 g (8.88 mmol) triethylamine to give the desired product after silica gel chromatography.

Synthesis of 14b: Method "F" was used with 1.33 g (2.12 mmol) of Compound 13b and 2.115 g (21.2 mmol) of isobutylamine. The yield was 1.5 g of material suitable for use in the next step (LC-MS (m/z) 699.2).

Synthesis of 15b: General method "H" was used with 1.5 g of Compound 14b, 0.697 g (6.557 mmol) sodium carbonate and 0.626 g (2.418 mmol) fluorenylmethyl chloroformate to yield 1.85 g of 15b (LC-MS (m/z) 919.65).

Synthesis of 1g: Method "I" was used with 2.1 g Compound 15b and 8.0 ml formic acid. The yield was 1.7 g (LC-MS (m/z) 846.4269).

EXAMPLE 8

Synthesis of Compound 1h

Synthesis of 10b: Method "F" was used with Compound 19 (2.41 g, 10.85 mmol); the amine was mono-CBZ protected 1,4 butane diamine. The intermediate secondary amine and excess mono-CBZ protected 1,4 butane diamine were isolated as an oil (3.5 g) and used in the next step with no further purification.

Synthesis of 11b: The mixture of 10b was subjected to method "G" using 1.31 ml (16.16 mmol) acryloyl chloride and 2.81 ml triethylamine. Chromatography yielded 1.02 g of 11b.

Synthesis of 12c: Method "F" was used with 1.05 g (2.59 mmol) of Compound 11b and 5.16 ml (51.92 mmol) of isobutylamine. Crude product (1.24 g) isolated by removal of the solvent and excess isobutylamine was suitable for use in the next step.

Synthesis of 13c: Method "G" was used with 12c (1.2 g), 0.38 ml (4.6 mmol) of acryloyl chloride, 0.8 ml (5.74 mmol) triethylamine, and a catalytic amount of DMAP.

Synthesis of 14c: The compound was prepared using method "F" with 1.05 g (1.975 mmol) of 13c and 3.925 g (39.5 mmol) of isobutylamine to give the intermediate amine product (1.27 g) suitable for use in the next step (LC-MS (m/z) 605.4).

Synthesis of 15c: General method "H" was performed on 14c to make the FMOC protected trimer using 1.27 g (2.1 mmol) 14c, 0.69 (6.5 mmol) sodium carbonate, and 0.60 g (2.36 mmol) fluorenylmethyl chloroformate to synthesize 15C (LC-MS (m/z) 827.4).

Synthesis of 1h: Method "I" was used with 1.5 g of 15c and 6 ml of formic acid. The yield was 1.16 g.

EXAMPLE 9

Synthesis of Compound 1i

Synthesis of 16a: General method "H" was used with 12a (4.43 g, 9.86 mmol), sodium carbonate (3.24 g, 30.58 mmol), and 9-fluorenylmethyl chloroformate (2.83 g, 11.1 mmol) to give 5.8 g of Compound 16a after purification (LC-MS (m/z) 672.3).

Synthesis of 1I: Method "I" was used with 7.4 g of 16a and 28 mL formic acid (LC-MS (m/z) 616.3027, retention time 21.648 min).

EXAMPLE 10

Synthesis of Compound 1j

Synthesis of 16b: General method "H" was used on 12c (1.02 g, 2.135 mmol), sodium carbonate (0.7 g, 6.6 mmol), and fluorenylmethyl chloroformate (0.61 g, 2.4 mmol) to give Compound 16b (1.12 g, LC-MS (m/z) 700.5).

Synthesis of 1j: Method "I" was used with 1.12 g of 16b and 5 ml of formic acid. The yield was 1.08 g (LC-MS (m/z) 644.4).

EXAMPLE 11

Synthesis of Compound 20

Rink—Lys(Boc) resin was treated with 3 cycles of general Method "K" using 1a. The oligopeptoid was then acetylated using method "L" and cleaved from the resin by method "M" to give 1.6 mg of 20.

EXAMPLE 12

Synthesis of Compound 21

Rink—Lys(Boc) resin was treated with 5 cycles of general Method "K" using 1a. The oligopeptoid was then acetylated using method "L" and cleaved from the resin by method "M" to give 5.8 mg of 21.

EXAMPLE 13

Synthesis of Compound 22

Rink—Lys(Boc) resin was treated with 6 cycles of general Method "K" using 1a. The oligopeptoid was then acetylated using method "L" and cleaved from the resin by method "M" to give 2.8 mg of 22.

EXAMPLE 14

Synthesis of Compound 23

Rink—Lys(Boc) resin was treated with 3 cycles of general Method "K" using 1b. The oligopeptoid was then acetylated using method "L" and cleaved from the resin by method "M" to give 12.1 mg of 23.

EXAMPLE 15

Synthesis of Compound 24

Rink—Lys(Boc) resin was treated with 4 cycles of general Method "K" using 1b. The oligopeptoid was then acetylated using method "L" and cleaved from the resin by method "M" to give 10.8 mg of 24.

EXAMPLE 16

Synthesis of Compound 25

Rink—Lys(Boc) resin was treated with 5 cycles of general Method "K" using 1b. The oligopeptoid was then acetylated using method "L" and cleaved from the resin by method "M" to give 8.6 mg of 25.

EXAMPLE 17

Synthesis of Compound 26

Rink—Lys(Boc) resin was treated with 6 cycles of general Method "K" using 1i. The oligopeptoid was then acetylated using method "L" and cleaved from the resin by method "M" to give 8.9 mg of 26.

EXAMPLE 18

Synthesis of Compound 27

Rink—Lys(Boc) resin was treated with 5 cycles of general Method "K" using 1d. The oligopeptoid was then acetylated using method "L" and cleaved from the resin by method "M" to give 15.0 mg of 27.

EXAMPLE 19

Synthesis of Compound 28

Rink—Lys(Boc) resin was treated with 7 cycles of general Method "K" using 1d. The oligopeptoid was then acetylated using method "L" and cleaved from the resin by method "M" to give 6.1 mg of 28.

EXAMPLE 20

Synthesis of Compound 29

Rink—Lys(Boc) resin was treated with 8 cycles of general Method "K" using 1d. The oligopeptoid was then acetylated using method "L" and cleaved from the resin by method "M" to give 6.5 mg of 29.

EXAMPLE 21

Synthesis of Compound 30

Rink—Lys(Boc) resin was treated with 5 cycles of general Method "K" using 1i. The oligopeptoid was then acetylated using method "L" and cleaved from the resin by method "M" to give 9.1 mg of 30.

EXAMPLE 22

Synthesis of Compound 31

Rink—Lys(Boc) resin was treated with 7 cycles of general Method "K" using 1i. The oligopeptoid was then acetylated using method "L" and cleaved from the resin by method "M" to give 4.3 mg of 31.

EXAMPLE 23

Synthesis of Compound 32

Rink—Lys(Boc) resin was treated with 8 cycles of general Method "K" using 1i. The oligopeptoid was then acetylated using method "L" and cleaved from the resin by method "M" to give 5.9 mg of 32.

EXAMPLE 24

Synthesis of Compound 33

Rink—Lys(Boc) resin was treated with 3 cycles of general Method "K" using 1f. The oligopeptoid was then acetylated using method "L" and cleaved from the resin by method "M" to give 4.5 mg of 33.

EXAMPLE 25

Synthesis of Compound 34

Rink—Lys(Boc) resin was treated with 4 cycles of general Method "K" using 1f. The oligopeptoid was then acetylated using method "L" and cleaved from the resin by method "M" to give 3.3 mg of 34.

EXAMPLE 26

Synthesis of Compound 35

Rink—Lys(Boc) resin was treated with 2 cycles of general Method "K" using 1g. The oligopeptoid was then acetylated using method "L" and cleaved from the resin by method "M" to give 1.6 mg of 35.

EXAMPLE 27

Synthesis of Compound 36

Rink—Lys(Boc) resin was treated with 5 cycles of general Method "K" using 12f. The oligopeptoid was then acetylated using method "L" and cleaved from the resin by method "M" to give 5.4 mg of 36.

EXAMPLE 28

Synthesis of Compound 37

Rink—Lys(Boc) resin was treated with 2 cycles of general Method "K" using 1h. The oligopeptoid was then acetylated using method "L" and cleaved from the resin by method "M" to give 8.6 mg of 37.

EXAMPLE 29

Synthesis of Compound 38

Rink—Lys(Boc) resin was treated with 3 cycles of general Method "K" using 1h. The oligopeptoid was then acetylated using method "L" and cleaved from the resin by method "M" to give 4.8 mg of 38.

EXAMPLE 30

Synthesis of Compound 39

Rink—Lys(Boc) resin was treated with 1 cycles of general Method "K" using 1h. The oligopeptoid was then acetylated using method "L" and cleaved from the resin by method "M" to give 17.0 mg of 39.

EXAMPLE 31

Synthesis of Compound 40

Rink—Lys(Boc) resin was treated with 2 cycles of general Method "K" using 1j. The oligopeptoid was then acetylated using method "L" and cleaved from the resin by method "M" to give 17 mg of 40.

EXAMPLE 32

Synthesis of Compound 41

Rink—Lys(Boc) resin was treated with 3 cycles of general Method "K" using 1j. The oligopeptoid was then acetylated using method "L" and cleaved from the resin by method "M" to give 6.0 mg of 41.

EXAMPLES 33-53

The minimal inhibitory concentration (MIC) for the peptoids was determined in sterile microtiter plates in a final volume of 200 µl using Trypticase Soy Broth (TSB; Difco Laboratories, Detroit, Mich.) as the growth medium. Serial two-fold dilutions of the peptoid stock were made in the plate wells such that concentrations ranged from 512 to 2 µg/ml in a volume of 100 µL. Each well was then inoculated with 100 µl of a dilute suspension of bacteria in TSB yielding a final concentration of $1 \times 10^4$ bacteria/ml. The final peptoid concentrations ranged from 256 µg/ml to 2 µg/ml. The assay plates were incubated at 37° C. for 24 hours inside a Bioscreen C microtitre plate reader (Thermo Labsystems; Vantaa, Finland). Optical Density (OD) of the medium at 600 nm was recorded every 20 minutes to monitor cell growth. The lowest concentration of peptoid preventing bacterial growth during the 24 hr period was defined as the MIC. The results of the experiments are shown in Table 1.

Table 1. Antibacterial activity of peptoids against *E. coli* ATCC 25922. The general structure for each of the Compounds 20 to 41 is represented by Formula V:

Formula V wherein 1) $A_1$-$A_i$ represent individual monomer units 1 to i, each having a side chain R or $R^1$ as defined by Formula I, and 2) n represents the number of repeating units ($A_1$-$A_i$). For Compounds 20 to 41, the number of individual monomer units ranges from 2 to 3 (i.e., ($A_1$-$A_2$) or ($A_1$-$A_2$-$A_3$)), and n ranges from 1 to 8. Abbreviations: Ac, acetyl; Lys, lysine. "Bz", "DMAP", "Ibu", "aminoethyl" and "aminobutyl" are R and $R^1$ groups according to Formula I as follows:

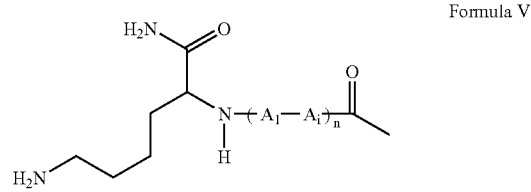

"Ibu"   "Bz"   "Aminoethyl"   "DMAP"   "Aminobutyl"

| Example No. | Compound No. | STRUCTURE | MIC (µg/ml) |
|---|---|---|---|
| 33 | 20 | Ac(Bz-DMAP-Ibu)$_3$-Lys-NH$_2$ | 128 |
| 34 | 21 | Ac(Bz-DMAP-Ibu)$_5$-Lys-NH$_2$ | 128 |
| 35 | 22 | Ac(Bz-DMAP-Ibu)$_6$-Lys-NH$_2$ | 128 |
| 36 | 23 | Ac(Bz-Ibu-DMAP)$_3$-Lys-NH$_2$ | 512 |
| 37 | 24 | Ac(Bz-Ibu-DMAP)$_4$-Lys-NH$_2$ | 128 |
| 38 | 25 | Ac(Bz-Ibu-DMAP)$_5$-Lys-NH$_2$ | 128 |
| 39 | 26 | Ac(Ibu-Aminoethyl)$_6$-Lys-NH$_2$ | 128 |
| 40 | 27 | Ac(Ibu-DMAP)$_5$-Lys-NH$_2$ | >512 |
| 41 | 28 | Ac(Ibu-DMAP)$_7$-Lys-NH$_2$ | >512 |
| 42 | 29 | Ac(Ibu-DMAP)$_8$-Lys-NH$_2$ | >512 |
| 43 | 30 | Ac(Ibu-Aminoethyl)$_5$-Lys-NH$_2$ | >256 |
| 44 | 31 | Ac(Ibu-Aminoethyl)$_7$-Lys-NH$_2$ | 128 |
| 45 | 32 | Ac(Ibu-Aminoethyl)$_8$-Lys-NH$_2$ | 256 |
| 46 | 33 | Ac(Ibu-Ibu-Aminoethyl)$_3$-Lys-NH$_2$ | >512 |
| 47 | 34 | Ac(Ibu-Ibu-Aminoethyl)$_4$-Lys-NH$_2$ | 256 |
| 48 | 36 | Ac(Ibu-Ibu-Aminoethyl)$_5$-Lys-NH$_2$ | 256 |
| 49 | 37 | Ac(Ibu-Ibu-Aminobutyl)$_2$-Lys-NH$_2$ | >512 |
| 50 | 38 | Ac(Ibu-Ibu-Aminobutyl)$_3$-Lys-NH$_2$ | >512 |
| 51 | 39 | Ac(Ibu-Ibu-Aminobutyl)$_1$-Lys-NH$_2$ | >512 |
| 52 | 40 | Ac(Ibu-Aminobutyl)$_2$-Lys-NH$_2$ | >512 |
| 53 | 41 | Ac(Ibu-Aminobutyl)$_3$-Lys-NH$_2$ | 512 |

EXAMPLE 54

Antimicrobial β-Peptoid Immobilization on Silk

Silk fiber is extracted three times with methylene chloride prior to use. β-Peptoid (10 mg of Compound 20) and silk fiber (100 mg) are suspended in 5.0 mL of 50 mM sodium phosphate buffer at pH 6.2. The mixture is shaken at 70° C. for 16 hrs. The mixture is allowed to cool to room temperature for 20 min, and the excess solution is decanted. The fiber is washed with distilled, deionized water (4×10 mL with 15 min agitation), and dried in an oven at 90° C. for 30 min. The biological activity of the fabric sample against *E. coli* ATCC #25922 is evaluated using the Shake Flask Test (see Example 4), and the log reduction in *E. coli* CFU/mL after 4 hours is determined.

EXAMPLE 55

Antimicrobial β-Peptoid Immobilization on EUPERGIT® Resin

The matrix of EUPERGIT® is a copolymerisate of methacrylamide, N,N'-methylene-bis(methacrylamide) and monomers containing oxirane groups. The oxirane groups function as the reactive components and covalently β-peptoids via their amino and sulfhydryl groups.

EUPERGIT® resin (100 mg EUPERGIT®, Sigma, 150 µm particle size) is charged into a polypropylene vial. β-Peptoid (10 mg of Compound 39) in 1 mL of 1 M phosphate buffer (pH 7.7) is added to the dry resin, followed by the addition of 1.5 mL of 1.0 M sodium phosphate buffer (pH 7.7). The mixture is shaken on a laboratory rotator at room temperature for 15 hr. The vial is then centrifuged and the supernatant is decanted. Phosphate buffer 0.1M (pH 7.7); 1.5 mL) is added to the resin; the resin is shaken for 30 min and then centrifuged and the buffer is decanted. This washing procedure is repeated two additional times. The washed resin is then shaken with a 20% ethanolamine solution in 1.0 M phosphate buffer (pH 7.7) at room temperature overnight. The resin is then washed four times with 0.1 M phosphate buffer (pH 7.7), followed by washing with water (4×). The biological activity of the sample against *E. coli* ATCC #25922 is evaluated using the Shake Flask Test (see Example 4), and the log reduction in *E. coli* CFU/mL after 4 hours is determined.

EXAMPLE 56

Antimicrobial β-Peptoid Immobilization on Polyurethane

Polyether polyurethane (400 mg, Elasthane™ 75 D, The Polymer Technology Group, Berkeley, Calif.) is dissolved in 0.5 mL of dimethylformamide. To this mixture is added 20 mg of Compound 22. The mixture is agitated on a vortexer, and the solution is drawn over a glass plate to form a polyurethane film.

EXAMPLE 57

Antimicrobial β-Peptoid Immobilization on Polyester

Polyester fabric (poly(ethylene terephthalate)) is immersed in a 10% sodium hydroxide solution for 90 min and then washed with deionized water. The fabric is then treated with a 10% hydrogen chloride solution for 20 min, washed with deionized water, and air-dried. The fabric is then extracted three times with methylene chloride.

The fabric (100 mg) is weighed into a 20 mL vial. β-Peptoid (Compound 44, 10 mg) in 5.0 mL of 50 mM sodium phosphate buffer (pH 5) is added to the vial, followed by 10 mg of N-(3-Dimethylaminopropyl)-N'-ethylcarbodiimide hydrochloride (EDC; Sigma-Aldrich, St. Louis, Mo.) hydrochloride. The mixture is shaken at room temperature for 5 hrs. The solution is decanted. The fabric is washed with distilled, deionized water (4×10 mL with 15 min agitation), and dried in an oven at 90° C. for 30 min.

EXAMPLE 58

Antimicrobial β-Peptoid Immobilization on Polyester

Polyester fabric (poly(ethylene terephthalate)) is immersed in a 10% sodium hydroxide solution for 90 min and then is washed with deionized water. The fabric is treated with a 10% hydrogen chloride solution for 20 min, washed with deionized water, and air-dried. The fabric is then extracted three times with methylene chloride.

The fabric (200 mg) is suspended in 20 mL 2 mM EDC and 5 mM 1-hydroxy-2,5-dioxo-3-pyrrolidinesulfonic acid, monosodium salt hydrate, in 0.1 M 2-(N-morpholino)ethane sulfonic acid buffer at pH 4.7. The mixture is stirred at room temperature for 1hr. The fabric is removed and is suspended in 4 mL of 0.1 M sodium phosphate buffer, pH 7.5. To this is added 10 mg of β-peptoid (Compound 39). The mixture is stirred at room temperature for four hours. The mixture is decanted and the fabric is washed with water (4×10 mL), and is oven dried at 60° C. for 1 hour.

EXAMPLE 59

Antimicrobial β-Peptoid Immobilization on Polyester

Polyester fabric (poly(ethylene terephthalate)) is immersed in a 10% sodium hydroxide solution for 90 min and then is washed with deionized water. The fabric is treated with a 10% hydrogen chloride solution for 20 min, washed with deionized water, and air-dried. The fabric is then extracted three times with methylene chloride.

The polyester fabric (50 mg) is immersed in 5 mL 50 mM phosphate buffer (pH 6.0). To this is added 5 mg of β-peptoid (Compound 44), EDC (10 mg) and HOBT (FW 153.2, 8 mg, 0.052 mmol). The mixture is stirred at room temperature for 4 hrs. The excess reagent is decanted, and the material is rinsed with ethanol (3×10 mL×15 minutes) followed by water (4×10 mL×15 minutes), and is dried in an oven at 90° C. for 30 min.

What is claimed is:

1. A β-peptoid consisting of Formula V:

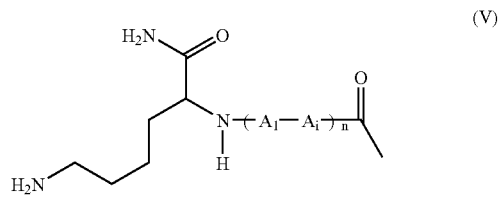

wherein n represents the number of repeating units of $(A_1-A_i)$ and ranges from 1 to 8;

$A_1-A_i$ represent individual monomer units 1 to i, wherein i is 2 or 3, $(A_1-A_i)$ is $(A_1-A_2)$ when i is 2 and $(A_1-A_i)$ is $(A_1-A_2-A_3)$ when i is 3, and each individual monomer unit is defined by Formula II:

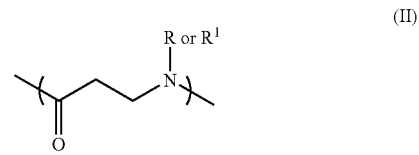

wherein

R is independently selected from the group consisting of benzyl (Bz), and isobutyl (Ibu), and $R^1$ is independently selected from the group consisting of dimethylaminopropyl (DMAP), aminoethyl and aminobutyl;

and wherein the β-peptoid is selected from the group consisting of:

$Ac(Bz-DMAP-Ibu)_3-Lys-NH_2$;
$Ac(Bz-DMAP-Ibu)_5-Lys-NH_2$;
$Ac(Bz-DMAP-Ibu)_6-Lys-NH_2$;
$Ac(Bz-Ibu-DMAP)_3-Lys-NH_2$;
$Ac(Bz-Ibu-DMAP)_4-Lys-NH_2$;
$Ac(Bz-Ibu-DMAP)_5-Lys-NH_2$;
$Ac(Ibu-Aminoethyl)_6-Lys-NH_2$;
$Ac(Ibu-DMAP)_5-Lys-NH_2$;
$Ac(Ibu-DMAP)_7-Lys-NH_2$;
$Ac(Ibu-DMAP)_8-Lys-NH_2$;
$Ac(Ibu-Aminoethyl)_5-Lys-NH_2$;
$Ac(Ibu-Aminoethyl)-_7-Lys-NH_2$;
$Ac(Ibu-Aminoethyl)_8-Lys-NH_2$;
$Ac(Ibu-Ibu-Aminoethyl)_3-Lys-NH_2$;
$Ac(Ibu-Ibu-Aminoethyl)_4-Lys-NH_2$;
$Ac(Ibu-Ibu-Aminoethyl)_5-Lys-NH_2$;
$Ac(Ibu-Ibu-Aminobutyl)_2-Lys-NH_2$;
$Ac(Ibu-Ibu-Aminobutyl)_3-Lys-NH_2$;
$Ac(Ibu-Ibu-Aminobutyl)_1-Lys-NH_2$;
$Ac(Ibu-Aminobutyl)_2-Lys-NH_2$; and
$Ac(Ibu-Aminobutyl)_3-Lys-NH_2$ Wherein "Ac" is the acetyl group of Formula V and "Lys-NH$_2$" is the lysinamide group of Formula V.

2. An antimicrobial composition comprising at least one β-peptoid according to claim 1.

3. An antimicrobial substrate comprising at least one β-peptoid according to claim 1 bound to or incorporated into the substrate.

4. An article comprising an antimicrobial substrate of claim 3 wherein the article is selected from the group consisting of a personal care item, an agricultural item, a cosmetic, a package, a food handling item, a food delivery item, a personal garment, a medical device, a personal hygiene item, an article intended for oral contact, a household item, a toy, and a liquid separation article.

5. A method for killing, inhibiting, or preventing the growth of at least one microbe, the method comprising contacting the microbe with an effective amount of the β-peptoid of claim 1.

6. A method for preparing a β-peptoid according to claim 1 comprising:
   i) synthesizing β-peptoid blocks of 2-5 monomers;
   ligating the β-peptoid blocks of step (i) by amide bond formation.

7. The method of claim 6 wherein identical β-peptoid blocks are ligated.

8. The method of claim 6 wherein non-identical β-peptoid blocks are ligated.

9. A method for preparing a β-peptoid according to claim 1 comprising:
   a) contacting t-butyl acrylate with a primary amine of the Formula R—NH$_2$ or R$^1$—NH$_2$, wherein R—NH$_2$ and R$_1$—NH$_2$ optionally have protecting groups and are defined according to steps (a) and (b) of claim 1, to form an aminoester;
   b) contacting the aminoester of step (a) with acryloyl chloride to form an N-substituted acrylamide;
   c) contacting the N-substituted acrylamide of step (b) with a primary amine according to the Formula R—NH$_2$ or R$^1$—NH$_2$, wherein R—NH$_2$ and R$^1$—NH$_2$ optionally have protecting groups and are defined according to steps (a) and (b) of claim 1, to form an aminoester;
   d) repeating steps (b) and (c) 0-4 times to form a β-peptoid oligomer;
   e) contacting the terminal secondary amine of the β-peptoid oligomer of step (d) with a protecting group precursor;
   f) contacting the β-peptoid oligomer of step (e) with an acid to form a β-peptoid block;
   g) optionally contacting a solid phase synthesis resin with a spacer group to form a spacer-derivatized resin;
   h) removing the terminal secondary protecting group from the spacer-derivatized resin of step (g);
   i) contacting the spacer-derivatized resin of step (h) with a β-peptoid block of step (f) to form a resin-bound β-peptoid intermediate;
   j) removing the terminal secondary amine from the resin-bound β-peptoid intermediate of step (i);
   k) contacting the resin of step (j) with a second β-peptoid block;
   l) repeating steps (j) and (k) 0-25 times until a β-peptoid of desired length is achieved;
   m) optionally removing the terminal secondary amine from the β-peptoid of step (l);
   n) optionally capping the β-peptoid of step (m);
   o) cleaving the β-peptoid of step (n) from the resin; and
   p) optionally purifying the cleaved β-peptoid of step (o).

10. A method for preparing an antimicrobial β-peptoid according to claim 1 comprising:
   a) contacting resin with acryloyl chloride and triethylamine to form an acrylated resin;
   b) contacting the acrylated resin of step (a) with a primary amine of the Formula R—NH$_2$ or R$^1$—NH$_2$, wherein R—NH$_2$ and R$^1$—NH$_2$ optionally have protecting groups and are defined according to steps (a) and (b) of claim 1;
   c) contacting the product of step (b) with acryloyl chloride and TEA;
   d) contacting the product of step (c) with a primary amine of the Formula R—NH$_2$ or R$^1$—NH$_2$, wherein R—NH$_2$ and R$^1$—NH$_2$ optionally have protecting groups and are defined according to steps (a) and (b) of claim 1;
   e) repeating steps (c) and (d) 0-5 times to form a β-peptoid oligomer;
   f) contacting the terminal secondary amine of the β-peptoid oligomer of step (e) with a protecting group precursor;
   g) contacting the β-peptoid oligomer of step (f) with an acid to form a β-peptoid block;
   g) cleaving the β-peptoid block from the resin;
   h) purifying the cleaved β-peptoid block;
   i) optionally contacting a solid phase synthesis resin with a spacer group to form a spacer-derivatized resin;
   j) removing the terminal secondary amine protecting group from the spacer-derivatized resin of step (i);
   k) contacting the spacer-derivatized resin of step (j) with a β-peptoid block of step (h) to form a resin-bound β-peptoid intermediate;
   l) removing the terminal secondary amine from the resin-bound β-peptoid intermediate of step (k);
   m) contacting the resin of step (l) with a second β-peptoid block;
   n) repeating steps (l) and (m) 0-25 times until a β-peptoid of desired length is achieved;
   o) optionally removing the terminal secondary amine from the β-peptoid of step (n);
   p) optionally capping the p-peptoid of step (o);
   q) cleaving the β-peptoid of step (p) from the resin; and
   r) optionally purifying the cleaved β-peptoid of step (q).

* * * * *